(12) United States Patent
Grayson

(10) Patent No.: US 11,862,446 B2
(45) Date of Patent: Jan. 2, 2024

(54) FUNCTIONALIZED CALIBRANTS FOR SPECTROMETRY AND CHROMATOGRAPHY

(71) Applicant: The Administrators of the Tulane Educational Fund, New Orleans, LA (US)

(72) Inventor: Scott M. Grayson, New Orleans, LA (US)

(73) Assignee: POLYMER FACTORY SWEDEN AB, Stockholm (SE)

(*) Notice: Subject to any disclaimer, the term of this patent is extended or adjusted under 35 U.S.C. 154(b) by 908 days.

(21) Appl. No.: 16/617,692

(22) PCT Filed: May 29, 2018

(86) PCT No.: PCT/US2018/034885
§ 371 (c)(1),
(2) Date: Nov. 27, 2019

(87) PCT Pub. No.: WO2018/222593
PCT Pub. Date: Dec. 6, 2018

(65) Prior Publication Data
US 2020/0105513 A1 Apr. 2, 2020

Related U.S. Application Data

(60) Provisional application No. 62/512,570, filed on May 30, 2017.

(51) Int. Cl.
*H01J 49/00* (2006.01)
*B01D 15/34* (2006.01)
(Continued)

(52) U.S. Cl.
CPC .......... *H01J 49/0009* (2013.01); *B01D 15/34* (2013.01); *C07C 69/30* (2013.01);
(Continued)

(58) Field of Classification Search
None
See application file for complete search history.

(56) References Cited

U.S. PATENT DOCUMENTS

2005/0037516 A1  2/2005  Schmucker et al.
2011/0240838 A1  10/2011  Debono et al.
(Continued)

FOREIGN PATENT DOCUMENTS

WO  2009/088461 A2  7/2009
WO  2009/136853 A1  11/2009
(Continued)

OTHER PUBLICATIONS

PCT International Search Report for PCT/US18/34885, dated Sep. 28, 2018.
(Continued)

*Primary Examiner* — Xiaoyun R Xu
(74) *Attorney, Agent, or Firm* — MCBEE MOORE & VANIK IP, LLC

(57) ABSTRACT

Calibrants and methods of making the same include using mixtures of multifunctional core compounds or multifunctional dendrimers that are functionalized to yield a set of discrete compounds which cover a range of collisional cross sections (CCSs) for calibrating ion mobility and variation in molecular weight to calibrate the mass to charge (m/z) measurements of mass spectrometry, as well as for calibrating tandem instruments that measure both dimensions. Methods of using the calibrants are also disclosed, such as in mass spectrometry.

20 Claims, 22 Drawing Sheets

(51) Int. Cl.
    *C07C 69/30*     (2006.01)
    *C07C 69/33*     (2006.01)
    *C07C 69/67*     (2006.01)
    *G01N 30/04*     (2006.01)
    *G01N 27/623*     (2021.01)

(52) U.S. Cl.
    CPC .............. *C07C 69/33* (2013.01); *C07C 69/67* (2013.01); *G01N 27/623* (2021.01); *G01N 30/04* (2013.01); *G01N 2030/042* (2013.01)

(56) References Cited

U.S. PATENT DOCUMENTS

2012/0210948 A1     8/2012     Furton et al.
2015/0132854 A1     5/2015     Grayson

FOREIGN PATENT DOCUMENTS

| WO | WO 2010/020361 | * | 2/2010 | .............. C08L 67/08 |
| WO | 2010/091109 A2 | | 8/2010 | |
| WO | 2017036545 A1 | | 3/2017 | |

OTHER PUBLICATIONS

Yamashita, K. et al., "Novel Calibrants for Accurate Mass Measurement in ESI-MS", Analytical Sciences, (2003), vol. 19: 1191-1193.

* cited by examiner

FUNCTIONALIZED CALIBRANTS FOR SPECTROMETRY AND CHROMATOGRAPHY

CROSS-REFERENCE TO RELATED APPLICATIONS

This application is the National Stage entry of International Application No. PCT/US18/34885, filed 29 May 2018, which claims priority to U.S. Provisional Application Ser. No. 62/512,570, filed 30 May 2017, the content of which is herein incorporated by reference in its entirety.

BACKGROUND

1. Field

The present disclosure relates to calibrants for spectrometry and/or chromatography that separate materials based on their sizes and shapes and methods for calibrating such spectrometry and/or chromatography.

2. Description of Related Art

Ion mobility spectrometry (IMS) is capable of separating molecules that may have the same mass to charge ratio (m/z) but different conformational arrangements, such as those in metabolomic, proteomics, peptidomics, and exposomic analyses. IMS has become an important analytical characterization technique because of recent advances in the field, specifically the incorporation of electrospray ionization (ESI) and matrix assisted laser desorption ionization (MALDI) sources to IMS and improvements in analytical resolution. The combination of ESI with high-resolution IMS systems has been shown to be an important characterization technique for a wide range of analytes (drugs, chemical warfare agents, peptides, and proteins). IMS is also extremely fast and can provide additional information to present technologies through coupling schemes with front end separations (i.e. liquid or gas chromatography) or back end characterizations (mass spectrometry (MS)), thereby allowing multi-dimensional sample characterization with increased sensitivity and no additional time needed.

Ion mobility-mass spectrometry (IM-MS) is an analytical technique that separates gas-phase ions based on their molecular weight (more specifically, their mass to charge ratio, m/z) and size/shape (more specifically, their collisional cross section (CCS)). In this method, ions are introduced into a drift tube. The application of a static uniform electric field then propels these ions in the direction of the applied field. The tube is filled with a drift gas, typically helium or nitrogen. The time taken for an ion to drift through the tube is related to its rotationally averaged cross-sectional area—that is, the area covered by a particle, or more simply its collision cross-section (CCS). Compact structures travel faster than more elongated (extended) ions, due to fewer interactions with the drift gas.

WO2017036545A1 discloses a method for determining the structure of a target carbohydrate by ion mobility-mass spectrometry in negative ionization mode. CCS estimations were performed using an established protocol and dextran as calibrant (Dextran MW=1000 and Dextran MW=5000). The calibrant and each sample were measured on a travelling wave Synapt instrument at five wave velocities in negative ion mode. Drift times where extracted from raw data by fitting a Gaussian distribution to the arrival time distribution of each ion and corrected for their m/z dependent flight time. CCS reference values of dextran were corrected for charge and mass and a logarithmic plot of corrected CCSs against corrected drift times was used as a calibration curve to estimate CCSs. One calibration curve was generated for every wave velocity and each ion polarity. The resulting five estimated CCSs for each sample ion were averaged.

There remains a need for calibrants that can provide a wider range for both the CCS and the m/z dimensions while exhibiting minimal dispersity in CCS dimension (narrow peak width) using spectrometry and/or chromatography to separate materials based on their sizes and shapes.

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. No feature of the invention is critical or essential unless it is expressly stated as being "critical" or "essential."

The solution to this technical problem is provided by the embodiments characterized in the claims.

SUMMARY

In an aspect, the present disclosure relates to compositions containing at least one calibrant compound or a salt thereof or cationic complex thereof, or anionic complex thereof, in which the at least one calibrant compound or the salt thereof or cationic complex thereof, or anionic complex thereof may include an alcohol or an amine functionalized core and peripheral functionalities.

In another aspect, the present disclosure relates to methods of manufacturing the composition of the present disclosure, including mixing two or more of the cores with at least one alcohol functionality, and subjecting the mixture to an esterification reaction.

In another aspect, the present disclosure relates to methods of manufacturing the composition of the present disclosure, including mixing two or more of the cores with at least one amine functionality, and subjecting the mixture to an amidation reaction.

In another aspect, the present disclosure relates to methods of calibrating a mass spectrometer, including providing the composition of the present disclosure comprising at least one calibrant compound or salt thereof or cationic complex thereof, or anionic complex thereof, ionizing the at least one calibrant compound to provide at least one charged ion, collecting mass spectrometry data from the at least one charged ion, and calibrating the mass spectrometer based on the mass spectrometry data.

In another aspect, the present disclosure relates to methods of calibrating an ion mobility spectrometer, including providing the composition of the present disclosure comprising at least one calibrant compound or salt thereof, or cationic complex thereof, or anionic complex thereof, ionizing at least one calibrant compound to provide at least one charged ion, collecting ion mobility data from at least one charged ion in a drift gas, and calibrating the ion mobility spectrometer based on the ion mobility data.

In another aspect, the present disclosure relates to methods of calibrating an ion mobility-mass spectrometer, including providing the composition of the present disclosure comprising at least one calibrant compound or salt thereof or cationic complex thereof, or anionic complex thereof, ionizing at least one calibrant compound to provide at least one charged ion, collecting ion mobility data in a drift gas and mass spectrometer data from the at least one charged ion, and calibrating the ion mobility-mass spectrometer based on the ion mobility data and the mass spectrometer data.

In another aspect, the present disclosure relates to methods of calibrating a light scattering spectrometer, including providing the composition of the present disclosure comprising at least one calibrant compound, dissolving the at least one calibrant compound to provide a solution of at least one calibrant compound, collecting light scattering data from at least one calibrant compound, and calibrating the light scattering spectrometer based on the light scattering data.

In another aspect, the present disclosure relates to methods of calibrating a size exclusion chromatograph, including providing the composition of the present disclosure comprising at least one calibrant compound or salt thereof or cationic complex thereof, or anionic complex thereof, dissolving at least one calibrant compound to provide a solution of at least one calibrant compound, collecting size exclusion data from at least one calibrant compound; and calibrating the size exclusion chromatograph based on the size exclusion data.

In another aspect, the present disclosure relates to methods of determining physical properties of a sample, including providing the composition of the present disclosure comprising at least one calibrant compound or salt thereof or cationic complex thereof, or anionic complex thereof, providing the sample, collecting physical data from at least one calibrant compound, calibrating an instrument capable of measuring the physical properties based on the physical data, and determining the physical properties of the sample.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION OF A PREFERRED EMBODIMENT

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

Wherever any of the phrases "for example," "such as," "including" and the like are used herein, the phrase "and without limitation" is understood to follow unless explicitly stated otherwise. Similarly, "an example," "exemplary" and the like are understood to be non-limiting.

The term "substantially" allows for deviations from the descriptor that do not negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" or "at least one" is understood, unless such interpretation is nonsensical in context.

Although a range of calibration sets have been explored for ion mobility characterization, they exhibit a relatively narrow range of m/z and CCS values. The calibration systems employed for ion mobility-mass spectrometry (IM-MS) have largely been those already explored for ESI-MS, including Ultramark, polyalanine (Poly-Ala), and tetra(alkyl) ammonium salts (TAA salts).

Figure 1:
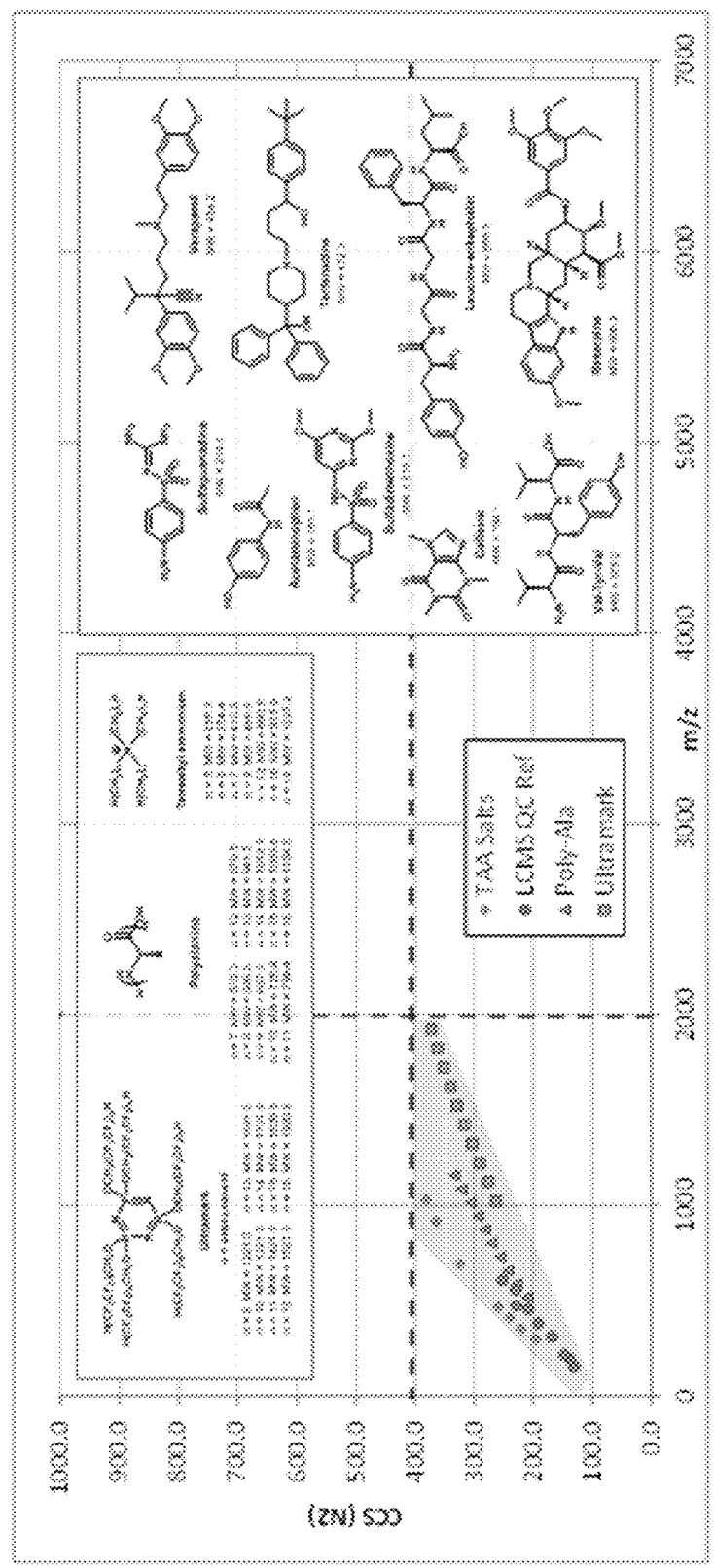
FIG. 1 shows current IM-MS calibrant options and their narrow range of m/z and CCS values using an ESI ionization source.

FIG. 1 shows that these compounds all have a similar degree of compactness (slope of CCS relative to m/z, and shown by the shaded area), with the fluorinated Ultramark calibrants exhibiting slightly more compact nature due to higher density of fluorine. The high proportion of ionizable atoms (e.g., O and N) in these calibrant systems result in limited m/z range for 1+ species, as higher masses tend to be multiply charged. For ions of these traditional calibrants in the 1+ charge state, the calibration range covered is limited. As shown by the small area occupied in the two-dimensional space by these two axes, these existing calibrants exhibit limited range in the CCS dimension (for $N_2$): 100-400 $Å^2$ (top CCS boundary), and limited range in the m/z dimension (typically m/z range: 0-2000) (right m/z boundary). Furthermore, they exhibit limited diversity in compactness (e.g. slope of CCS relative to m/z).

Therefore, there is a need for IM-MS calibrants that can overcome these limitations. The calibrants should provide a wider range for both the CCS and the m/z dimensions while exhibiting minimal dispersity in CCS dimension (narrow peak width). Additionally, the calibrants should be compatible with both positive and negative ion modes, should be technically simple to use, and should exhibit long shelf-lives.

In an aspect, the present disclosure relates to compositions containing at least one calibrant compound, or cationic complex thereof, or anionic complex thereof, in which the at least one calibrant compound or the salt thereof or cationic complex thereof, or anionic complex thereof, may include an alcohol or an amine functionalized core and peripheral functionalities.

The at least one calibrant compound or the salt thereof or cationic complex thereof, or anionic complex thereof, may include at least one core with at least one alcohol functionality, which may be selected from the group consisting of mono-functional cores, di-functional cores, tri-functional cores, tetra-functional cores, penta-functional cores, hexa-functional cores, octa-functional cores, and dendrimer-based cores comprising a plurality of alcohol functionalities.

For example, mono-functional cores with at least one alcohol functionality may be selected from the group consisting of methanol, ethanol, 1-propanol, 2-propanol, 1-butanol, 2-butanol, 3-methyl-1-butanol, 3-methyl-2-butanol, 2-methyl-1-butanol, and 2,2-dimethyl 1-propanol; di-functional cores may be selected from the group consisting of ethylene glycol, 1,2-propane diol, 1,3-propane diol, 1,2-butane diol, 1,3-butane diol, 1,4-butane diol, 2,3-butane diol, 1,2-pentane diol, 1,5-pentane diol, 1,2-hexane diol, and 1,6-hexane diol; tri-functional cores may be selected from the group consisting of 1,2,4-butane triol, 1,2,6-butane triol, 1,1,1-tris-(hydroxymethyl)ethane, and 1,1,1-tris-(hydroxymethyl)propane; tetra-functional cores may be selected from the group consisting of pentaerythritol, erythritol, and threitol; penta-functional cores may be selected from the group consisting of xylitol, arabinitol, arabitol, adonitol, and triglycerol; hexa-functional cores may be selected from the group consisting of dipentaerythritol, allitol, dulcitol, iditol, talitol, sorbitol, galactitol, and mannitol; octafunctional core may be tripentaerythritol; and dendrimer-based cores may contain at least one layer of bis-MPA repeating units bonding to any one of mono-functional cores, di-functional cores, tri-functional cores, tetra-functional cores, penta-functional cores, hexa-functional cores, and/or octa-functional cores by esterification.

The at least one calibrant compound or the salt thereof or cationic complex thereof, or anionic complex thereof, may include at least one core with at least one amine functionality, which may be selected from the group consisting of mono-functional cores, di-functional cores, tri-functional cores, tetra-functional cores, and dendrimer-based cores comprising a plurality of amine functionalities.

For example, mono-functional cores with at least one amine functionality may be selected from the group consisting of methylamine, ethylamine, 1-propylamine, 2-propamine, 1-butylamine, 2-butylamine, and tert-butylamine; di-functional cores may be selected from the group consisting of ethylene diamine, 1,2-propane diamine, 1,3-propane diamine, 1,2-butane diamine, 1,3-butane diamine, 1,4-butane diamine, 2,3-butane diamine, 1,5-pentane diamine, 1,6-hexane diamine, and 1,7-heptane diamine; tri-functional cores may be selected from the group consisting of 2,2'-diaminoethylamine, bis(hexamethylene) triamine, triazine, and tris(2-aminoethyl)amine; tetra-functional cores may be selected from the group consisting of 3,3'diaminobenzidine, triethylenetetramine, and hexamethylenetetramine; and dendrimer-based cores may be selected from the group consisting of polyamidoamine, polypropylene imine, and polytriazine dendrimers.

In another aspect, the present disclosure relates to compositions containing at least two calibrant compounds or salts thereof or cationic complex thereof, or anionic complex thereof, in which the at least two calibrant compounds or the salts thereof or cationic complex thereof, or anionic complex thereof, may contain the alcohol or amine functionalized cores and the peripheral functionalities.

In another aspect, the present disclosure relates to methods of manufacturing the composition of the present disclosure, including mixing one, two, three, four, five, six, or more of the at least one core with at least one alcohol functionality, and subjecting the mixture to an esterification reaction.

In another aspect, the present disclosure relates to methods of manufacturing the composition of the present disclosure, including mixing one, two, three, four, five, six, or more of the at least one core with at least one amine functionality, and subjecting the mixture to an amidation reaction.

Compositions of the present disclosure may be used to calibrate any instruments that can measure mass, size, shape, and/or collisional cross section area (CCS) of molecules in a gas phase.

In another aspect, the present disclosure relates to methods of calibrating a mass spectrometer, including providing the composition of the present disclosure, ionizing the at least one calibrant compound to provide at least one charged ion, collecting mass spectrometry data from the at least one charged ion, and calibrating the mass spectrometer based on the mass spectrometry data.

The at least one charged ion may be singly-charged or multi-charged ion. Mass spectrometry data may contain a mass to charge ratio (m/z) of the at least one charged ion. The mass to charge ratio (m/z) of the at least one charged ion may be from about 1 m/z to about 15000 m/z, from about 1 m/z to about 14000 m/z, from about 1 m/z to about 13000 m/z, from about 1 m/z to about 12000 m/z, from about 1 m/z to about 11000 m/z, from about 1 m/z to about 10000 m/z, from about 1 m/z to about 9000 m/z, from about 1 m/z to about 9500 m/z, from about 1 m/z to about 9000 m/z, from about 1 m/z to about 8500 m/z, from about 1 m/z to about 8000 m/z, from about 10 m/z to about 8000 m/z, from about 100 m/z to about 8000 m/z, from about 250 m/z to about 8000 m/z, from about 500 m/z to about 8000 m/z, from about 750 m/z to about 8000 m/z, from about 1000 m/z to about 8000 m/z, from about 1500 m/z to about 8000 m/z, from about 1700 m/z to about 8000 m/z, from about 2000 m/z to about 8000 m/z, from about 2500 m/z to about 8000 m/z, from about 3000 m/z to about 8000 m/z, from about 3500 m/z to about 8000 m/z, from about 4000 m/z to about 8000 m/z, from about 4500 m/z to about 8000 m/z, from about 5000 m/z to about 8000 m/z, or from about 5500 m/z to about 8000 m/z, from about 1 m/z to about 7500 m/z, from about 1 m/z to about 7000 m/z, from about 1 m/z to about 6500 m/z, from about 1 m/z to about 6000 m/z, from about 10 m/z to about 6000 m/z, from about 50 m/z to about 6000 m/z, from about 100 m/z to about 6000 m/z, from about 250 m/z to about 6000 m/z, from about 500 m/z to about 6000 m/z, from about 750 m/z to about 6000 m/z, from about 1000 m/z to about 6000 m/z, from about 1500 m/z to about 6000 m/z, from about 2000 m/z to about 6000 m/z, from about 2500 m/z to about 6000 m/z, from about 3000 m/z to about 6000 m/z, from about 3500 m/z to about 6000 m/z, from about 4000 m/z to about 6000 m/z, from about 4500 m/z to about 6000 m/z, from about 5000 m/z to about 6000 m/z, or from about 5500 m/z to about 6000 m/z.

In an embodiment, the mass to charge ratio (m/z) of the at least one charged ion may be from about 1 m/z to about 50 m/z, from about 50 m/z to about 100 m/z, from about 100 m/z to about 150 m/z, from about 150 m/z to about 200 m/z, from about 200 m/z to about 250 m/z, from about 250 m/z to about 300 m/z, from about 300 m/z to about 350 m/z, from about 350 m/z to about 400 m/z, from about 400 m/z to about 450 m/z, from about 450 m/z to about 500 m/z, from about 500 m/z to about 550 m/z, from about 550 m/z to about 600 m/z, from about 600 m/z to about 700 m/z, from about 700 m/z to about 800 m/z, from about 800 m/z to about 900 m/z, from about 900 m/z to about 1000 m/z, from about 1000 m/z to about 1100 m/z, from about 1100 m/z to about 1200 m/z, from about 1200 m/z to about 1300 m/z, from about 1300 m/z to about 1400 m/z, from about 1400 m/z to about 1500 m/z, from about 1500 m/z to about 1600 m/z, from about 1600 m/z to about 1700 m/z, from about 1700 m/z to about 1800 m/z, from about 1800 m/z to about 1900 m/z, from about 1900 m/z to about 2000 m/z, from about 2000 m/z to about 2100 m/z, from about 2100 m/z to about 2200 m/z, from about 2200 m/z to about 2300 m/z, from about 2300 m/z to about 2400 m/z, from about 2400 m/z to about 2500 m/z, from about 2500 m/z to about 2600 m/z, from about 2600 m/z to about 2700 m/z, from about 2700 m/z to about 2800 m/z, from about 2800 m/z to about 2900 m/z, from about 2900 m/z to about 3000 m/z, from about 3000 m/z to about 3100 m/z, from about 3100 m/z to about 3200 m/z, from about 3200 m/z to about 3300 m/z, from about 3300 m/z to about 3400 m/z, from about 3400 m/z to about 3500 m/z, from about 3500 m/z to about 3600 m/z, from about 3600 m/z to about 3700 m/z, from about 3700 m/z to about 3800 m/z, from about 3800 m/z to about 3900 m/z, from about 3900 m/z to about 4000 m/z, from about 4000 m/z to about 4250 m/z, from about 4250 m/z to about 4500 m/z, from about 4500 m/z to about 4750 m/z, from about 4750 m/z to about 5000 m/z, from about 5000 m/z to about 5250 m/z, from about 5250 m/z to about 5500 m/z, from about 5500 m/z to about 5750 m/z, from about 5750 m/z to about 6000 m/z, from about 6000 m/z to about 6250 m/z, from about 6250 m/z to about 6500 m/z, from about 6500 m/z to about 6750 m/z, from about 6750 m/z to about 7000 m/z, from about 7000 m/z to about 7500 m/z, from about 7500 m/z to about 8000 m/z, from about 8000 m/z to about 8500 m/z, from about 8500 m/z to about 9000 m/z, from about 9000 m/z to about 9500 m/z, from about 9500 m/z to about 10,000 m/z, from about 10,000 m/z to about 11,000 m/z, from about 11,000 m/z to about 12,000 m/z, from about 12,000 m/z to about 13,000 m/z, from about 13,000 m/z to about 14,000 m/z, from about 14,000 m/z to about 15,000 m/z.

The mass spectrometry may be selected from the group consisting of accelerator mass spectrometry, isotope ratio mass spectrometry, MALDI-TOF, SELDI-TOF, electrospray ionization (ESI)-mass spectrometry, thermal ionization-mass spectrometry, and spark source mass spectrometry, and the mass spectrometer may be selected from the group of spectrometers useful for performing said mass spectrometry.

In another aspect, the present disclosure relates to methods of calibrating an ion mobility spectrometer, including providing the composition of the present disclosure, ionizing the at least one calibrant compound to provide at least one charged ion, introducing the at least one charged ion into the ion mobility spectrometer, collecting ion mobility data from the at least one charged ion in a drift gas, and calibrating the ion mobility spectrometer based on the ion mobility data.

The at least one charged ion may be singly-charged or multi-charged. The ion mobility data may contain a collision cross section (CCS) value of the at least one charged ion. The collision cross section (CCS) value of the at least one charged ion may be from about 10 $Å^2$ to about 1500 $Å^2$, from about 10 $Å^2$ to about 1400 $Å^2$, from about 10 $Å^2$ to about 1300 $Å^2$, from about 10 $Å^2$ to about 1200 $Å^2$, from about 10 $Å^2$ to about 1100 $Å^2$, about 10 $Å^2$ to about 1000 $Å^2$, from about 10 $Å^2$ to about 900 $Å^2$, from about 100 $Å^2$ to about 900 $Å^2$, from about 150 $Å^2$ to about 900 $Å^2$, from about 150 $Å^2$ to about 850 $Å^2$, from about 150 $Å^2$ to about 800 $Å^2$, from about 150 $Å^2$ to about 750 $Å^2$, from about 150 $Å^2$ to about 700 $Å^2$, from about 150 $Å^2$ to about 650 $Å^2$, from about 150 $Å^2$ to about 600 $Å^2$, from about 200 $Å^2$ to about 1000 $Å^2$, from about 200 $Å^2$ to about 950 $Å^2$, from about 200 $Å^2$ to about 900 $Å^2$, from about 200 $Å^2$ to about 850 $Å^2$, from about 200 $Å^2$ to about 800 $Å^2$, from about 200 $Å^2$ to about 750 $Å^2$, from about 200 $Å^2$ to about 700 $Å^2$, from about 200 $Å^2$ to about 650 $Å^2$, from about 200 $Å^2$ to about 600 $Å^2$, from about 200 $Å^2$ to about 550 $Å^2$, from about 200 $Å^2$ to about 500 $Å^2$, from about 200 $Å^2$ to about 450 $Å^2$, from about 200 $Å^2$ to about 400 $Å^2$, from about 200 $Å^2$ to about 350 $Å^2$, from about 200 $Å^2$ to about 300 $Å^2$, from about 200 $Å^2$ to about 250 $Å^2$, from about 10 $Å^2$ to about 10 $Å^2$, from about 10 $Å^2$ to about 50 $Å^2$, from about 10 $Å^2$ to about 100 $Å^2$, from about 10 $Å^2$ to about 110 $Å^2$, from about 10 Å² to about 120 Å², from about 10 Å² to about 130 Å², from about 10 Å² to about 140 Å², from about 10 Å² to about 150 Å², from about 10 Å² to about 160 Å², from about 10 Å² to about 170 Å², from about 10 Å² to about 180 Å², from about 10 Å² to about 190 Å², or from about 10 Å² to about 200 Å².

In an embodiment, the collision cross section (CCS) value of the at least one charged ion may be from about 10 Å² to about 20 Å², from about 20 Å² to about 30 Å², from about 30 Å² to about 40 Å², from about 40 Å² to about 50 Å², from about 50 Å² to about 60 Å², from about 60 Å² to about 70 Å², from about 70 Å² to about 80 Å², from about 80 Å² to about 90 Å², from about 90 Å² to about 100 Å², from about 100 Å² to about 110 Å², from about 110 Å² to about 120 Å², from about 120 Å² to about 130 Å², from about 130 Å² to about 140 Å², from about 140 Å² to about 150 Å², from about 150 Å² to about 160 Å², from about 160 Å² to about 170 Å², from about 170 Å² to about 180 Å², from about 180 Å² to about 190 Å², from about 190 Å² to about 200 Å², from about 200 Å² to about 225 Å², from about 225 Å² to about 250 Å², from about 250 Å² to about 275 Å², from about 275 Å² to about 300 Å², from about 300 Å² to about 325 Å², from about 325 Å² to about 350 Å², from about 350 Å² to about 375 Å², from about 375 Å² to about 400 Å², from about 400 Å² to about 425 Å², from about 425 Å² to about 450 Å², from about 450 Å² to about 475 Å², from about 475 Å² to about 500 Å², from about 500 Å² to about 525 Å², from about 525 Å² to about 550 Å², from about 550 Å² to about 575 Å², from about 575 Å² to about 600 Å², from about 600 Å² to about 625 Å², from about 625 Å² to about 650 Å², from about 650 Å² to about 675 Å², from about 675 Å² to about 700 Å², from about 700 Å² to about 725 Å², from about 725 Å² to about 750 Å², from about 750 Å² to about 775 Å², from about 775 Å² to about 800 Å², from about 800 Å² to about 850 Å², from about 850 Å² to about 900 Å², from about 900 Å² to about 950 Å², from about 950 Å² to about 1000 Å², from about 1000 Å² to about 1100 Å², from about 1100 Å² to about 1200 Å², from about 1200 Å² to about 1300 Å², from about 1300 Å² to about 1400 Å², or from about 1400 Å² to about 1500 Å².

The drift gas may be selected from the group consisting of helium, nitrogen, argon, and carbon dioxide.

In another aspect, the present disclosure relates to methods of calibrating an ion mobility-mass spectrometer, including providing the composition of the present disclosure, ionizing the at least one calibrant compound to provide at least one charged ion, introducing the at least one charged ion into the ion mobility-mass spectrometer, collecting ion mobility data in a drift gas and mass spectrometer data from the at least one charged ion, and calibrating the ion mobility-mass spectrometer based on the ion mobility data and the mass spectrometer data.

In another aspect, the present disclosure relates to methods of calibrating a light scattering spectrometer, including providing the composition of the present disclosure, dissolving the at least one calibrant compound to provide a solution of the at least one calibrant compound, introducing the solution of the at least one calibrant compound into the light scattering spectrometer, collecting light scattering data from the at least one calibrant compound, and calibrating the light scattering spectrometer based on the light scattering data. The light scattering data may contain the size of the at least one calibrant compound in the solution.

In another aspect, the present disclosure relates to methods of calibrating a size exclusion chromatograph, including providing the composition of the present disclosure, dissolving the at least one calibrant compound to provide a solution of the at least one calibrant compound, introducing the solution of the at least one calibrant compound into the size exclusion chromatograph, collecting size exclusion data from the at least one calibrant compound; and calibrating the size exclusion chromatograph based on the size exclusion data. The size exclusion data may contain the size of the at least one calibrant compound in the solution.

In another aspect, the present disclosure relates to methods of determining physical properties of a sample, including providing the composition of the present disclosure, providing the sample, collecting physical data from the at least one calibrant compound, calibrating an instrument capable of measuring the physical properties based on the physical data, and determining the physical properties of the sample. The physical properties of the sample may include mass, size, shape, and/or collisional cross section area of the sample in a drift gas. The instrument may be selected from the group consisting of mass spectrometer, ion mobility spectrometer, ion mobility-mass spectrometer, light scattering spectrometer, size exclusion chromatograph, and a combination thereof.

Embodiments of the present disclosure include novel calibrants and methods of making these calibrants that contain multifunctional cores and/or dimethylolpropionic acid (bis-MPA), i.e.,

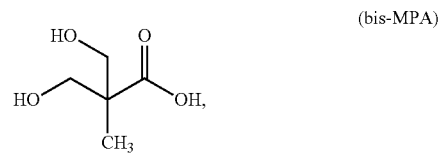

(bis-MPA)

based polyester dendrimers. These core molecules or dendrimers may be functionalized on their periphery to prepare a series of singular discrete compounds with exact molecular weights and well-defined sizes. These functionalized cores and dendrimers may then be used as IMS calibrants. Each compound within a sample set may be composed of a core molecule with at least one alcohol functionality, or at least one amine functionality. Each of these alcohol or amine functionalities can then be coupled with an activated carboxylic acid to yield multiple ester or amide bonds.

Functionalized cores or dendrimers (the latter based on the bis-MPA monomer) are prepared as singular discrete compounds that may exhibit a wider range of CCS and m/z values. In some embodiments, CCS values of greater than 800 Å², and m/z values of in excess of 5500 (for singly charges species) can be measured, more than doubling the range of the existing common calibrants.

To achieve higher CCS values, embodiments of the present disclosure may include the addition of alkyl chains onto the periphery of the cores to make "star-shaped" calibrants (with multiple alkyl arms). Fatty acids varying from short chains to long chains are coupled with the multifunctional cores or dendrimers. Though the addition of long alkyl chains may not significantly increase the propensity for charging (ease of complexation with cations), it does increase the size substantially, and therefore yields extended conformations with high CCS values but modest m/z values.

In one embodiment, the present disclosure provides functionalized polyester dendrimers based on bis-MPA monomer that may be modified by esterification of their peripheral functionalities in order to prepare a set of singular, discrete compounds that may exhibit a wider range of CCS and m/z values. In particular, CCS values in excess of 800 Å$^2$, and m/z values of in excess of 5500 (for singly charges species) can be measured, more than doubling the range of existing calibrants.

In another embodiment, the present disclosure provides functionalized core molecules by reacting activated carboxylic acid derivatives with the alcohol and/or amine functionalities of the multifunctional cores. A set of discrete compounds may be generated that expand the available range of m/z calibration points as well as CCS calibration points for IM-MS characterization.

For example, multifunctional core may have a formula I: X—[OH]$_n$, in which n is an integer from 3 to 20, and X is a core comprised of alkane, ether, ester, amine, and/or amide functionalities or generations of alkane, ether, ester, amine, and/or amide dendrimers. Non-limiting examples of X—[OH]$_n$ cores are shown in Table 1.

TABLE 1

| X | n | Core Symbol | Core Structure |
|---|---|---|---|
| alkyl | 3 | C | |
| | 4 | D | |
| | 5 | E | |
| ether | 6 | F | |
| | 8 | H | |
| amine | 3 | | |
| | 4 | | |

TABLE 1-continued

| X | n | Core Symbol | Core Structure |
|---|---|---|---|
| | 5 | | [structure: N center with two CH2OH groups and two -CH2CH2OH arms, plus tris-like branch] |
| G1 dendrimer | 6 | C1 | [structure: pentaerythritol core esterified with three 2,2-bis(hydroxymethyl)propionic acid units] |
| | 8 | D1 | [structure: pentaerythritol core esterified with four bis-MPA units] |
| | 10 | E1 | [structure: xylitol/sugar-like core esterified with five bis-MPA units] |

TABLE 1-continued

| X | n | Core Symbol | Core Structure |
|---|---|---|---|
|  | 12 | F1 | 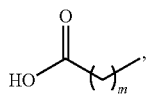 |

X—[OH]$_n$ may be reacted with carboxylic acid derivatives, such as those of Formula II:

(Formula II)

where m is an integer from 1 to 30.

For example, carboxylic acid derivatives may be selected from the group consisting of methanoic (formic) acid, ethanoic (acetic) acid, propanoic (proprionic) acid, butanoic (butyric) acid, pentanoic (valeric) acid, hexanoic (caprylic) acid, heptanoic (enanthic) acid, octanoic (caprylic) acid, nonanoic (pelargonic) acid, decanoic (capric) acid, undecanoic acid, dodecanoic (lauric) acid, tridecanoic acid, tetradecanoic (myristic) acid, pentadecanoic acid, hexadecanoic (palmitic acetic) acid, heptadecanoic (margaric acetic) acid, octadecanoic (stearic acetic) acid, nonadecanoic acid, eicosanoic (arachidic) acid, heneicosanoic acid, docosanoic (behenic) acid, tetracosanoic (lignoceric) acid, hexacosanoic (cerotic) acid, octacosanoic (montanic) acid, and triacosanoic (melissic) acid.

In addition, X—[OH]$_n$ may be reacted with carboxylic acid derivatives that include a hydrocarbon chain that may contain one or more branching points, one or more double bond, and/or one or more triple bond, such as arachidonic acid, cis-13-docosenoic acid, cis-11-eicosenoic acid, elaidic acid, linoleic acid, linolenic acid, linolelaidic acid, myristoleic, oleic acid, palm itoleic acid, petroselenic acid, and cis-15-tetracosenoic acid.

A synthetic scheme for esterification of multifunctional cores or multifunctional dendrimer cores is shown below:

(Formula III)

$$X\text{---}[OH]_n \xrightarrow[\text{DCC, DMAP}]{\text{HO}\overset{O}{\underset{}{\|}}\text{C}\text{---}(\ )_m} X\text{---}\left[O\overset{O}{\underset{}{\|}}\text{C}\text{---}(\ )_m\right]_n,$$

wherein m=2, 6, 10, 16, or 20, n=3 to 20, and X is a core comprised of alkane, ether, ester, amine, and/or amide functionalities or generations of alkane, ether, ester, amine, and/or amide dendrimers (e.g., as shown in Table 1). These reactions may be achieved using dicyclohexylcarbodiimide (DCC) and 4-dimethylaminopyridine (DMAP) as a catalyst.

Figure 2:
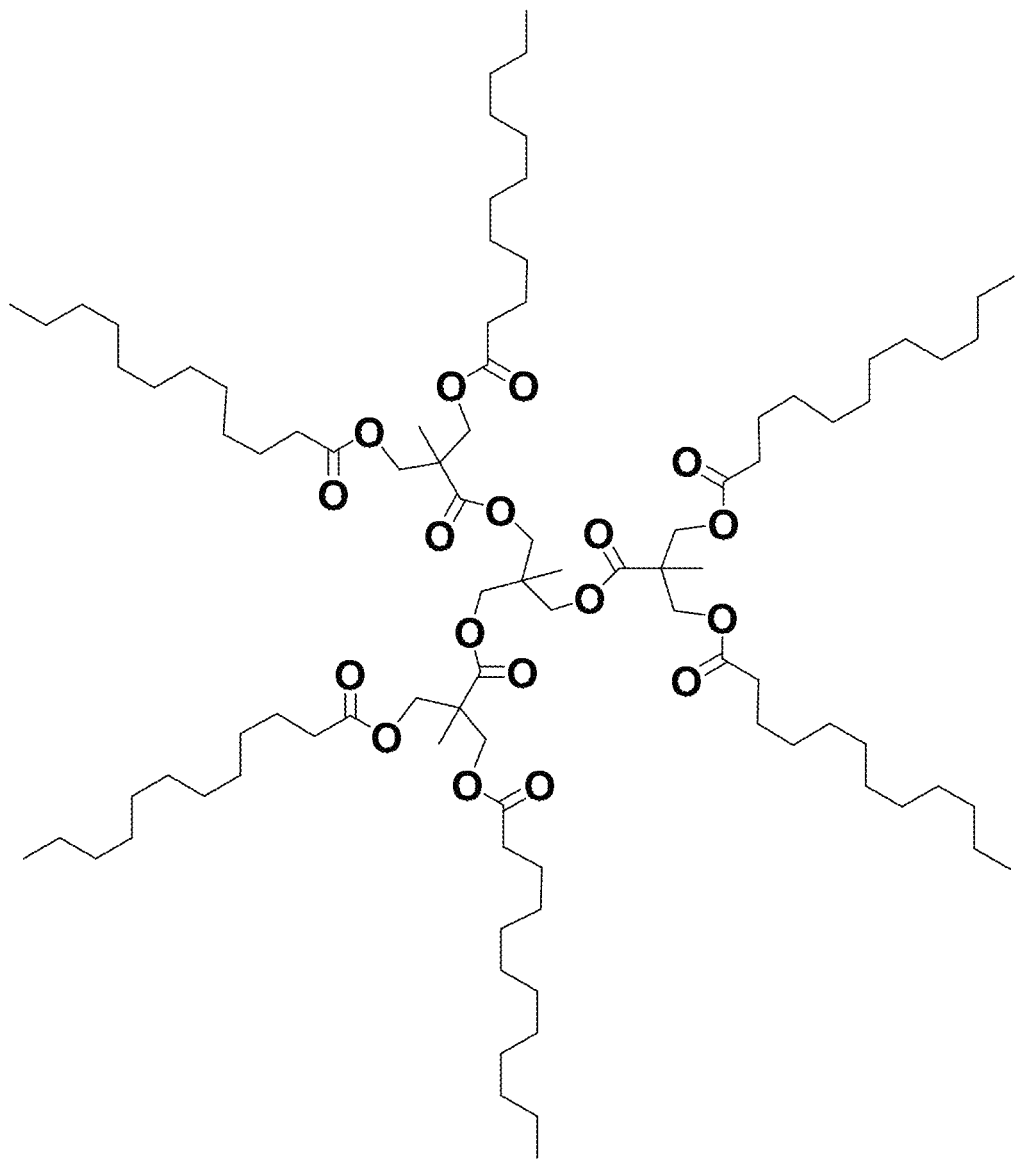
FIG. 2 shows a representative calibrant molecule in accordance with one embodiment of the present disclosure.

FIG. 2 shows a calibrant based on a hexafunctional alcohol core C1 (n=6) (a bis-MPA dendrimer) that has been esterified with dodecyl (lauryl) esters to yield a compound with an exact molecular weight and a well-defined size.

To evaluate the performance of the calibrants of the present disclosure in IM-MS, a mixture of the calibrants of the present disclosure shown in Table 2 and the existing standards, e.g., TAA salts, LCMS QC Ref, Poly-Ala, Ultramark, and SphericalCal Mix, are compared.

TABLE 2

| Calibrant Mixture | Core Symbols | Cores Esterified with 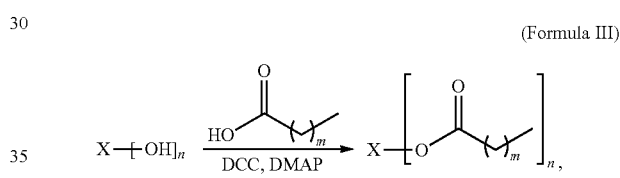 | Cores Esterified with |
|---|---|---|---|
| IMS 004 C-F | C, D, E, F | m = 4 | NA |
| IMS 008 C-F | C, D, E, F | m = 8 | NA |
| IMS 012 C-F | C, D, E, F | m = 12 | NA |
| IMS 018 C1-F1 | C1, D1, E1, F1 | m = 18 | NA |

TABLE 2-continued

| Calibrant Mixture | Core Symbols | Cores Esterified with HO-C(=O)-(CH2)m-CH3 | Cores Esterified with HO-C(=O)-C6H(Dy)- |
|---|---|---|---|
| IMS 018 H | H | m = 18 | NA |
| IMS 022 C-F | C, D, E, F | m = 22 | NA |
| IMS 100 C-F | C, D, E, F | NA | y = 0 |
| IMS 103 C-F | C, D, E, F | NA | y = 3 |
| IMS 103 C1-F1 | C1, D1, E1, F1 | NA | y = 3 |
| IMS 103 H | H | NA | y = 3 |

Figure 3:
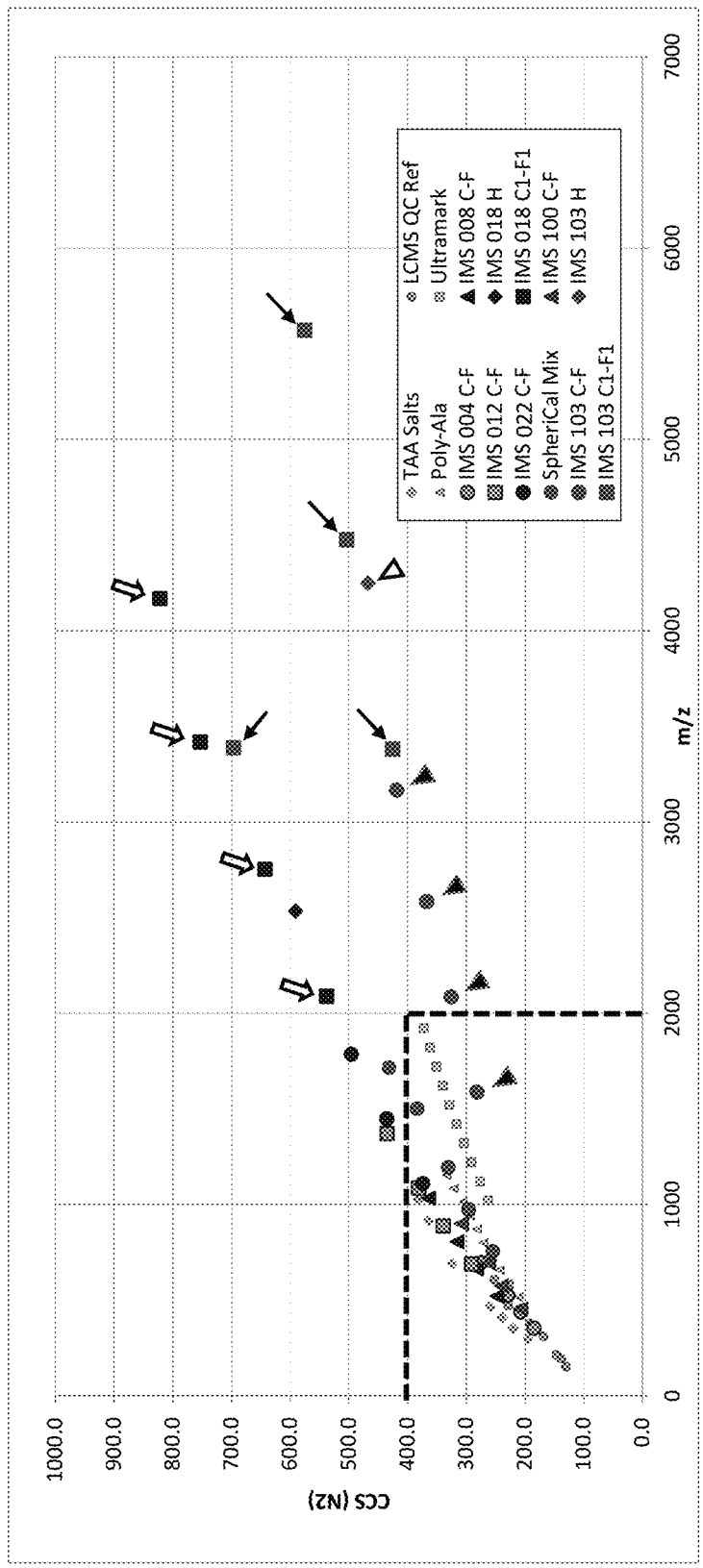
FIG. 3 shows various embodiments of the present disclosure compared to existing calibrant options. Calibrants of the present disclosure may contain multifunctional cores and/or dendrimers with pendant fatty ester groups, providing higher CCS values and multifunctional cores and/or dendrimers with halogenated aromatics, showing higher m/z values and lower CCS values. In particular, CCS values above 800 Å$^2$, and m/z values of in excess of 5500 (for singly charges species) can be measured, more than doubling the range exhibited by existing calibrants.

FIG. 3 shows that the addition of alkyl chains, e.g., from 4-carbon chain (IMS 004) to 22-carbon chain (IMS 022), onto cores and dendrimers provides a more extended conformation, and hence higher CCS values relative to m/z, (with values as high as 813 Å², e.g., 18-carbon chain IMS 018 C1-F1 as indicated by open arrows), than the existing standards, e.g., TAA salts, LCMS QC Ref, Poly-Ala, and Ultramark, as shown in FIG. 1. The SpheriCal standards exhibit a trend in compactness similar to the existing standards, but may extend the CCS range just beyond 400 Å². All data correspond to $Na^+$ adducts.

To achieve higher m/z, an embodiment of the present disclosure may include the incorporation of multiple halogen atoms into the calibrant compositions. Achieving high m/z can be a challenge in mass spectrometry because increases in the mass (m) tends to also increase the ability to carry charge (z). However, certain elements (e.g. iodine "I") have a high atomic mass (A.M.=127) but may not have an increased propensity to carry charge (e.g. relative to elements like O, atomic mass=16, and N, atomic mass=14). To a lesser extent, the same may be true for fluorine (A.M.=19). Therefore, an embodiment of the present disclosure may include compounds with high I (or F) content that can exhibit very high masses in low charge states (hence high m/z) as well as very compact conformation with modest CCS values, despite high m/z values.

For example, X—[OH]$_n$ may be reacted with carboxylic acid derivatives, such as those of Formula IV:

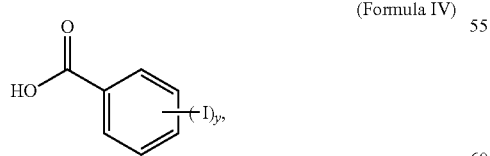

(Formula IV)

in which y is an integer from 0 to 5.

For example, carboxylic acid derivatives may be selected from the group consisting of benzoic acid, 2-iodo benzoic acid, 3-iodo benzoic acid, 4-iodo benzoic acid, 2,3-diiodo benzoic acid, 2,4-diiodo benzoic acid, 2,5-diiodo benzoic acid, 2,6-diiodo benzoic acid, 3,4-diiodo benzoic acid, 3,5-diiodo benzoic acid, 2,3,4-triiodo benzoic acid, 2,3,5-triiodo benzoic acid, 2,3,6-triiodo benzoic acid, 3,4,5-triiodo benzoic acid, 2,3,4,5-tetraiodobenzoic acid, 2,3,4,6-tetraiodobenzoic acid, 2,3,5,6-tetraiodobenzoic acid, and 2,3,4,5,6-pentaiodobenzoic acid.

A synthetic scheme for esterification of multifunctional cores or multifunctional dendrimer cores is shown below:

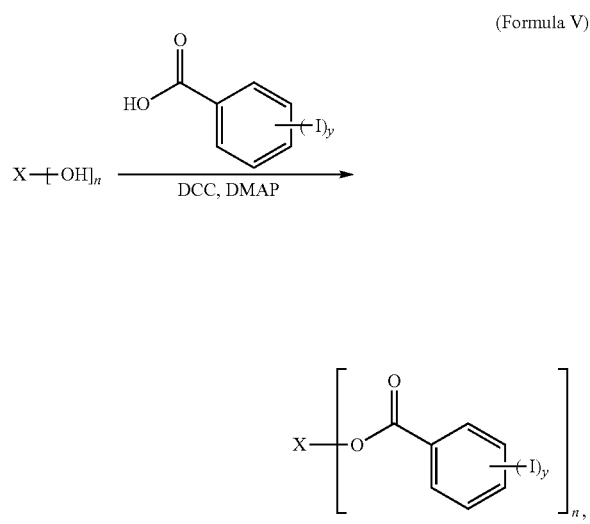

(Formula V)

e.g., y=0 or 3, n=3 to 20, and X as defined above. These reactions may be carried out in the presence of dicyclohexylcarbodiimide (DCC) and 4-dimethylaminopyridine (DMAP).

Table 3 shows the chemical structures of some calibrants with triiodobenzoate functionalized cores in accordance with some embodiments of the present disclosure.

TABLE 3
| X | n | Core Symbol | Core Structure | Calibrant Structure (Calibrant Symbol) |
|---|---|---|---|---|
| alkyl | 3 | C | 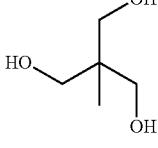 | 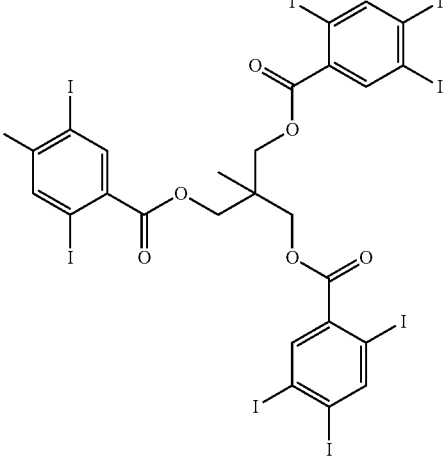<br>(IMS 103 C) |
|  | 4 | D | 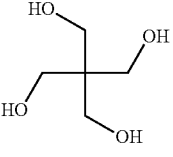 | 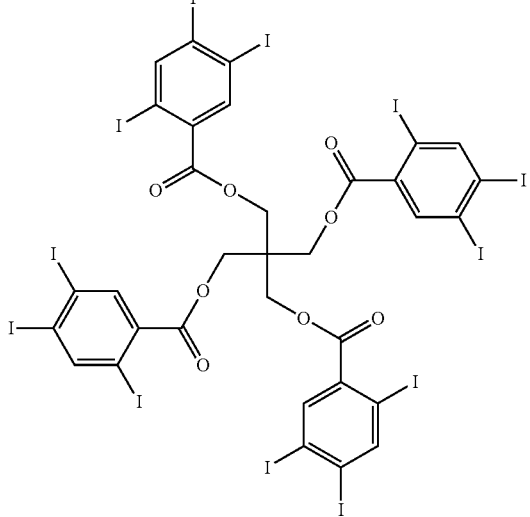<br>(IMS 103 D) |
|  | 5 | E | 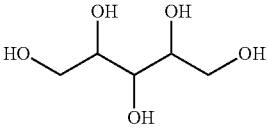 | 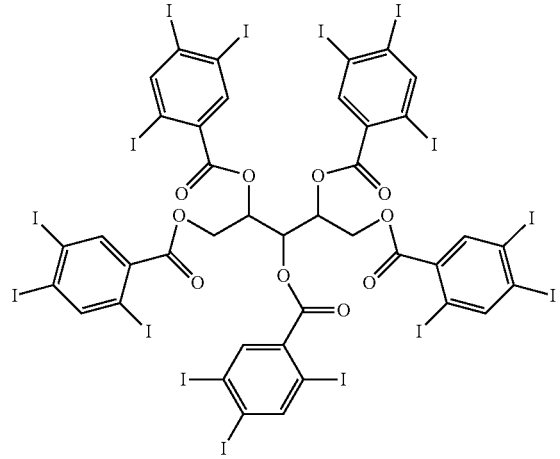<br>(IMS 103 E) |

TABLE 3-continued

| X | n | Core Symbol | Core Structure | Calibrant Structure (Calibrant Symbol) |
|---|---|---|---|---|
| ether | 6 | F | [structure of bis(trimethylolpropane) ether type hexaol core] | [hexaiodobenzoate ester calibrant] (IMS 103 F) |
| | 8 | H | [octaol core structure with three ether linkages] | [octa-triiodobenzoate ester calibrant] (IMS 103 H) |

TABLE 3-continued
| X | n | Core Symbol | Core Structure | Calibrant Structure (Calibrant Symbol) |
|---|---|---|---|---|
| G1 dendrimer | 6 | C1 | 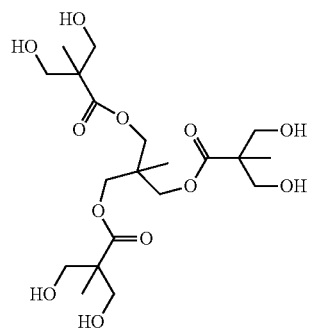 [SMILES: CC(COC(=O)C(C)(CO)CO)(COC(=O)C(C)(CO)CO)COC(=O)C(C)(CO)CO] | 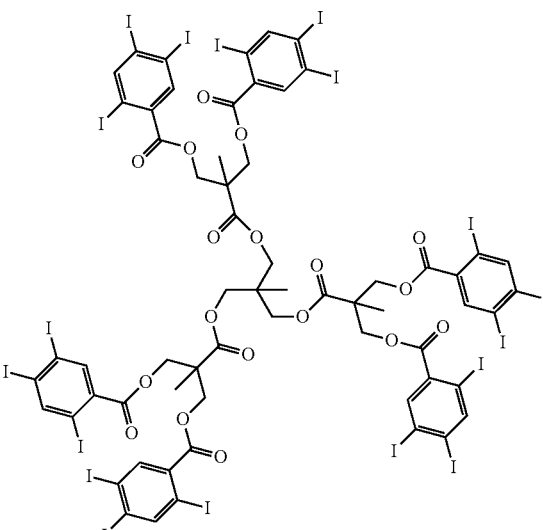<br>(IMS 103 C1) |
| | 8 | D1 | 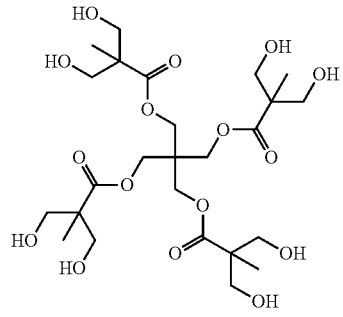 [SMILES: CC(CO)(CO)C(=O)OCC(COC(=O)C(C)(CO)CO)(COC(=O)C(C)(CO)CO)COC(=O)C(C)(CO)CO] | 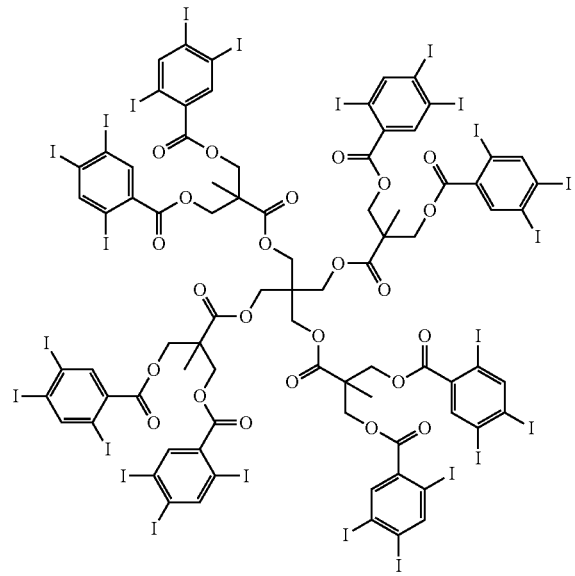<br>(IMS 103 D1) |

TABLE 3-continued

| X | n | Core Symbol | Core Structure | Calibrant Structure (Calibrant Symbol) |
|---|---|---|---|---|
| | 10 | E1 | *[chemical structure]* | *[chemical structure]* (IMS 103 E1) |
| | 12 | F1 | *[chemical structure]* | *[chemical structure]* (IMS 103 F1) |

FIG. 3 shows that halogenated aromatics, e.g., triiodobenzoate functionalized core (IMS 103 C-F, IMS 103 C1-F1, and IMS 103 H), exhibit higher mass to size ratio, hence higher m/z, lower CCS values, and an overall more compact trend line than the existing standards, e.g., TAA salts, LCMS QC Ref, Poly-Ala, and Ultramark, as shown in FIG. 1. This may increase the m/z values in the 1+ charge state from below 2000 to as high as 5571, with a CCS of only 576 Å$^2$, e.g., IMS 103 C1-F1 (as indicated by arrows). The slope of IMS 103 C1-F1 together with IMS 103 C-F (as indicated by arrow heads) and IMS 103 H (as indicated by open arrow head) is smaller than that of IMS 004-024, indicating that IMS 103 calibrants are more compact than IMS 004-024 calibrants. IMS 103 calibrants achieve very high masses in low charge states (hence high m/z) as well as very compact conformation with modest CCS values, despite high m/z values.

Size dispersity refers to the range of sizes that a single compound may exhibit. If the compounds are flexible, they may exhibit both very compact and very extended conformations. Embodiments of the present disclosure may include branched cores that lead to structures, which are more architecturally compact and therefore lack the ability to exhibit a wide range of shapes. This is in contrast, for example, to a long linear compound, which may exhibit either compact (wadded up) or extended (more elongated linear) conformations.

Figure 4:
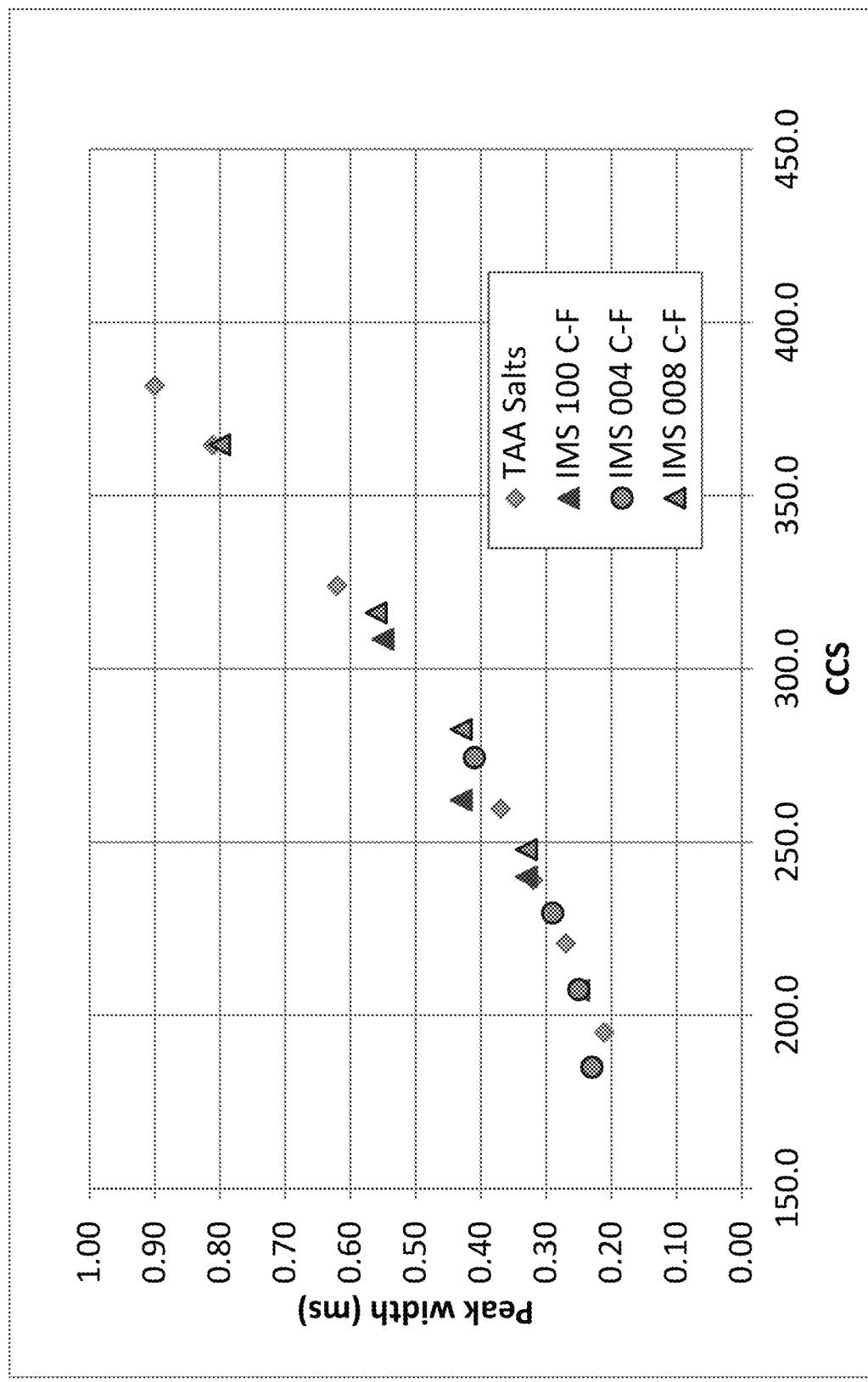
FIG. 4 shows measurements of CCS values for selected calibrants, in accordance with the present disclosure.

FIG. 4 shows that the observed peak width in the CCS dimension is a function of both instrument resolution and the dispersities of conformation, which are sampled by the molecule in the gas phase. The series of dendrimers, e.g., IMS 100 C-F (see Example 7), IMS 004 C-F (with 4-carbon chain), and IMS 008 C-F (with 8-carbon chain), exhibit CCS dispersities as narrow as those observed by other calibrants, such as the trialkyl ammonium salts (TAA salts). The conformational dispersity of the dendrimer calibrants of the present disclosure may be as narrow as those measured for other calibrants.

Embodiments of the present disclosure may include calibrants that exhibit the ability to complex with a range of cations and/or anions to achieve mass spectra and ion mobility spectra in both positive and negative ion modes.

Figure 5:
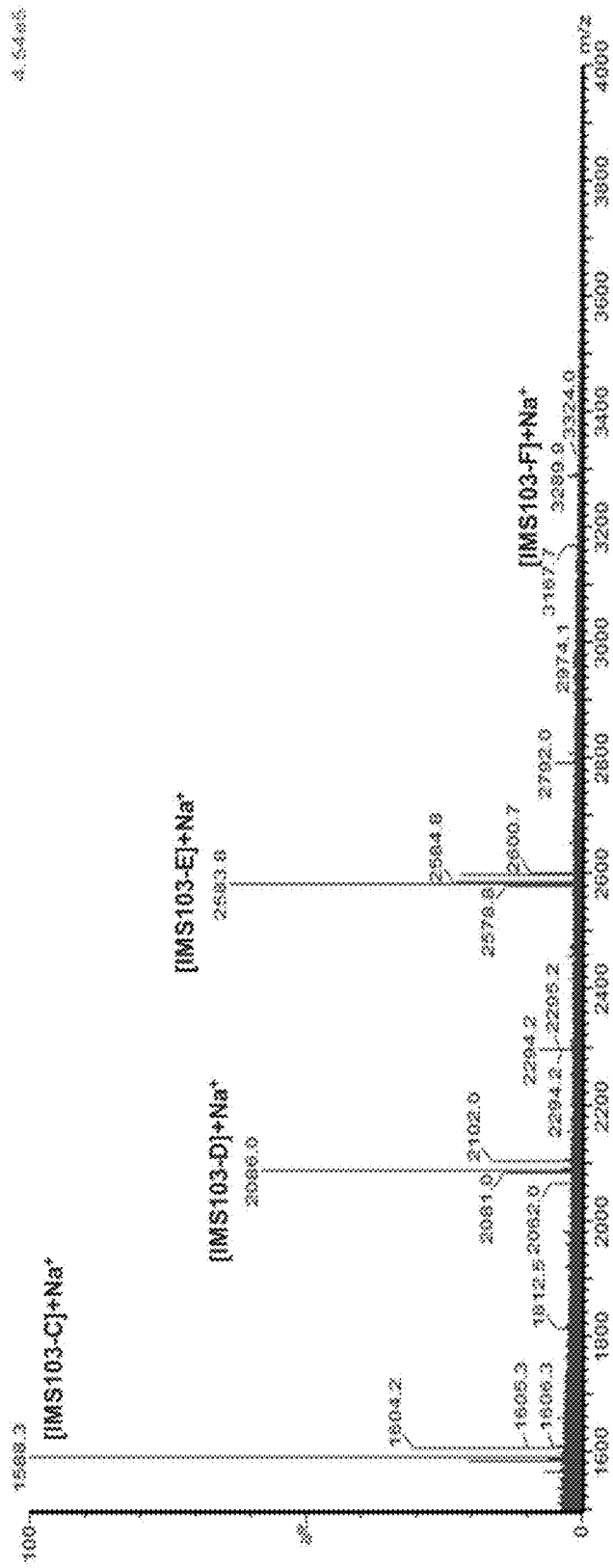
FIG. 5 shows MALDI-TOF MS data for calibrants in accordance with the present disclosure.

FIG. 5 shows an analysis in the positive mode of ionization, in which data for calibrations can be achieved, as long as the appropriate salt is used. In positive ion mode, with 0.1% sodium formate used as a cation source in 0.1% formic acid, IMS103 (IMS103-C, IMS103-D, IMS103-E, and IMS103-F) yields sodiated adducts.

Figure 6:
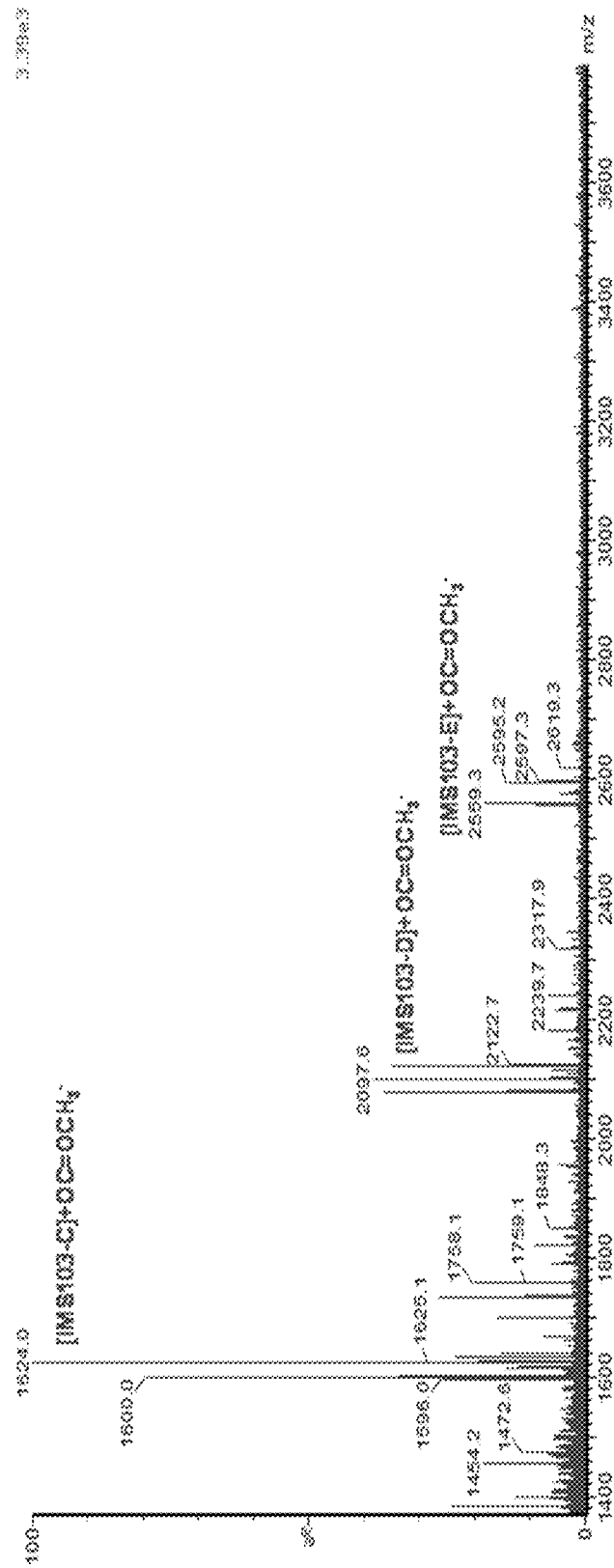
FIG. 6 shows MALDI-TOF MS data for calibrants in accordance with the present disclosure.

FIG. 6 shows an analysis in the negative mode of ionization, in which data for calibrations can be achieved, as long as the appropriate salt is used. In negative ion mode, with 1% ammonium acetate used as an anion source in 1% ammonia, IMS103 (IMS103-C, IMS103-D, and IMS103-E) yields acetate adducts.

In another embodiment of the invention, compounds exhibiting a range of compactness, from high CCS and low m/z (more extended) to low CCS and high m/z (more compact) are disclosed. By tuning the compactness of the calibrants (e.g., varying peripheral groups from long, extended linear fatty acids, to short, mass-dense iodinated aromatic rings) a larger area of the ion mobility mass spectrometry graph may be covered by calibration points, rather than a single linear trend as observed by most of the existing calibrations systems.

EXAMPLES

Example 1

Butanoate Functionalized Cores (IMS 004)

To a round bottom flask was added one or more of the following "core" compounds: ethylene glycol ("B"), tris (hydroxymethyl)ethane ("C"), pentaerythritol ("D"), xylitol ("E"), dipentaerythritol ("F"), tripentaerythritol "H"), or bis-MPA dendrimers made from the above cores. These were dissolved in tetrahydrofuran. 1.1 molar equivalents (per —OH of the hydroxyl terminated cores or dendrimers) of butanoic acid were added to the solution of cores. To these reagents were added 1.2 molar equivalents (per —OH of the hydroxyl terminated cores or dendrimers) of dicyclohexylcarbodiimide and 0.1 molar equivalents (per —OH of hydroxyl-terminated core or of dendrimer) of 4-dimethyl-aminopyridine (DMAP).

The reaction mixture was stirred vigorously for approximately 12 hours at standard temperature and pressure. The reaction was monitored by MALDI-TOF MS to confirm completion of the reaction for each of the cores present in the reaction. After complete esterification is observed by MALDI-TOF MS, the flask contents were transferred to a separatory funnel, diluted with dichloromethane, extracted twice with 1M aqueous $NaHSO_4$ (sodium bisulfate) and extracted twice with 1M aqueous $NaHCO_3$ (sodium bicarbonate). The organic layer was reduced in vacuo to concentrate the sample. A MALDI-TOF MS spectra of the purified product confirmed the purity of the mixture of esterified products and is shown in FIG. 7.

Figure 7:
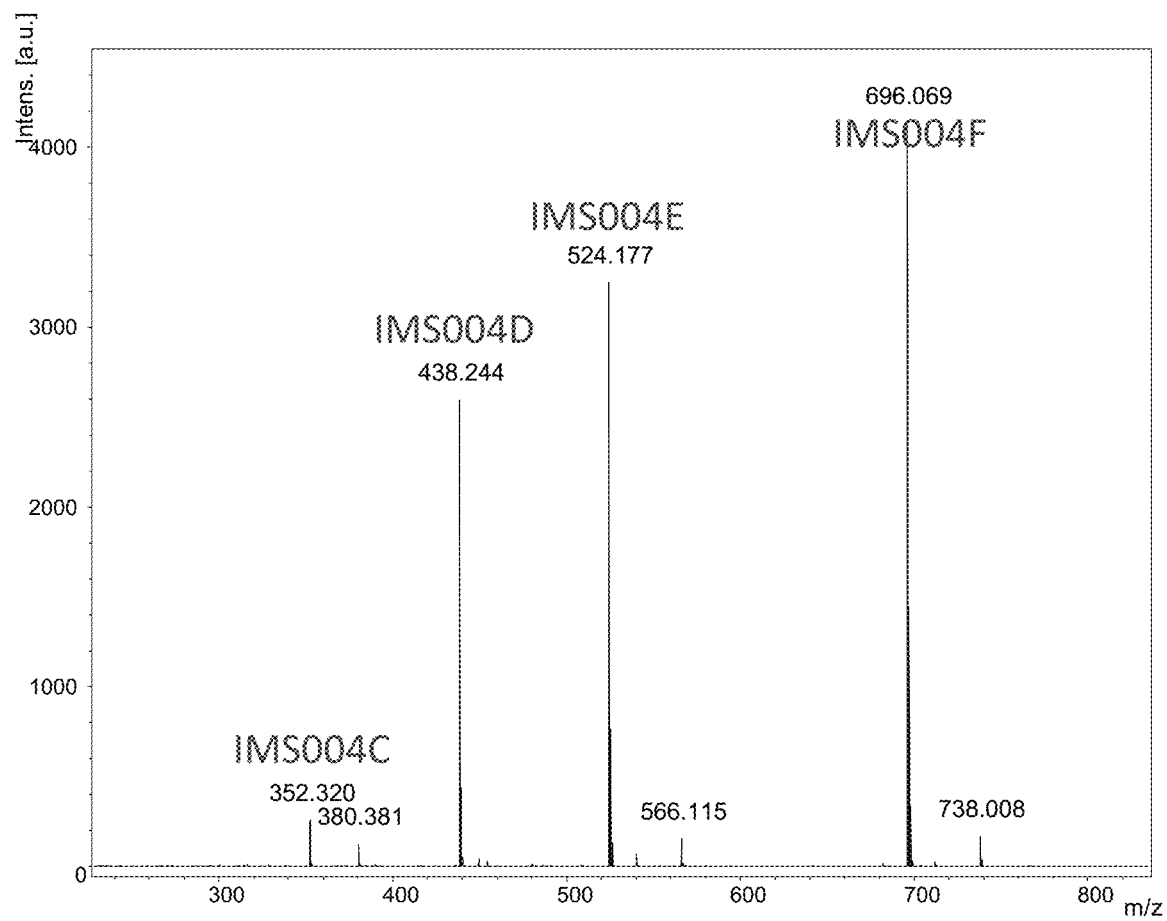
FIG. 7 shows MALDI-TOF MS data for calibrants in accordance with an embodiment of the present disclosure.

FIG. 7 shows MALDI-TOF MS data for IMS 008 C-F, the product of octanoic acid functionalization of cores C, D, E, and F.

Example 2

Octanoate Functionalized Cores (IMS 008 C-F)

To a round bottom flask was added one or more of the following "core" compounds: tris(hydroxymethyl)ethane ("C"), pentaerythritol ("D"), xylitol ("E"), dipentaerythritol ("F") made from the above cores. These were dissolved in tetrahydrofuran. 1.1 molar equivalents (per —OH of the hydroxyl terminated cores or dendrimers) of Octanoic Acid were added to the solution of cores. To these reagents were added 1.2 molar equivalents (per —OH of the hydroxyl terminated cores or dendrimers) of dicyclohexylcarbodiimide and 0.1 molar equivalents (per —OH of hydroxyl-terminated core or of dendrimer) of 4-dimethylaminopyridine (DMAP).

The reaction mixture was stirred vigorously for approximately 12 hours at standard temperature and pressure. The reaction was monitored by MALDI-TOF MS to determine completion of the reaction for each of the cores present in the reaction. After complete esterification is observed by MALDI-TOF MS, the flask contents were transferred to a separatory funnel, diluted with dichloromethane, extracted twice with 1M aqueous $NaHSO_4$ (sodium bisulfate) and extracted twice with 1M aqueous $NaHCO_3$ (sodium bicarbonate). The organic layer was reduced in vacuo to concentrate the sample. A MALDI-TOF MS spectra of the purified product confirmed the purity of the mixture of esterified products and is shown in FIG. 8.

Figure 8:
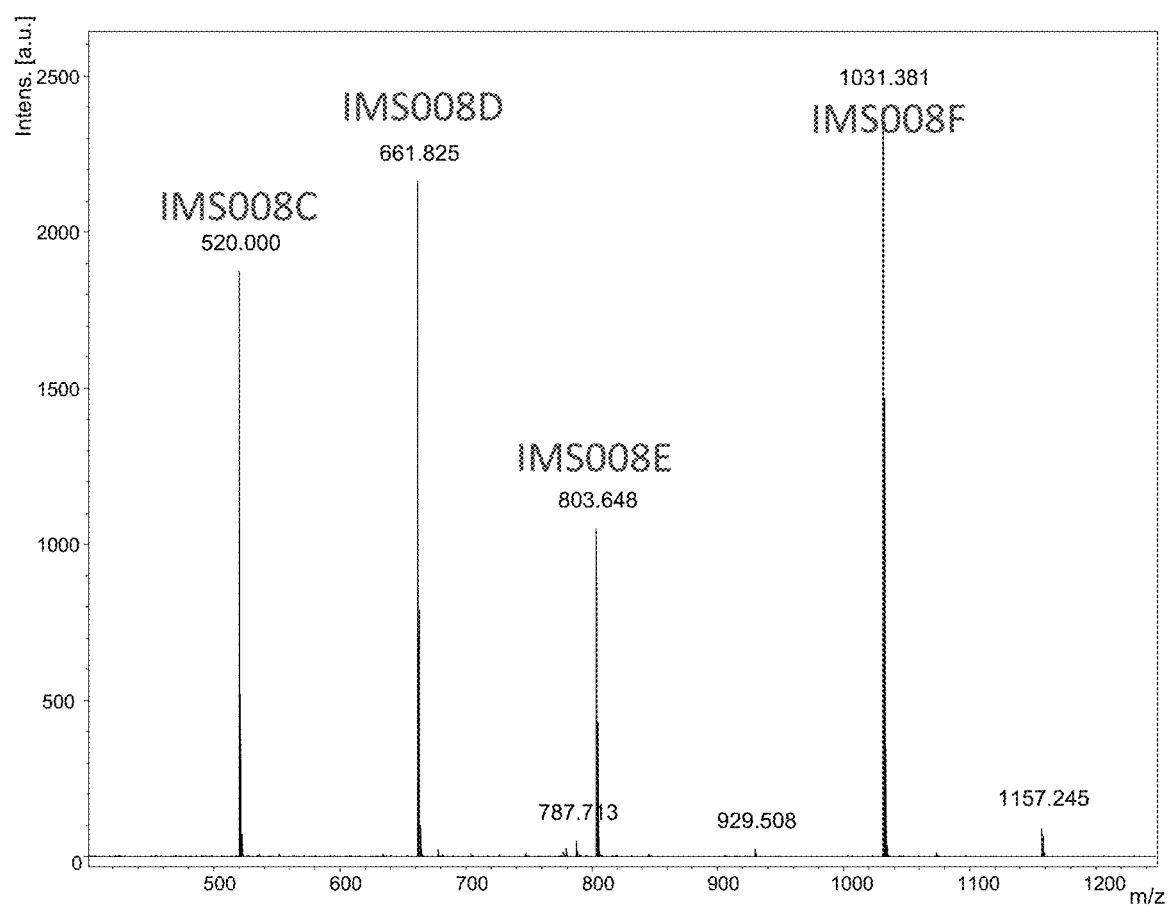
FIG. 8 shows MALDI-TOF MS data for calibrants in accordance with another embodiment of the present disclosure.

FIG. 8 shows MALDI-TOF MS data for IMS 008 C-F, the product of octanoic acid functionalization of cores C, D, E, and F.

Example 3

Dodecanoate Functionalized Cores (IMS 012 C-F)

Figure 9:
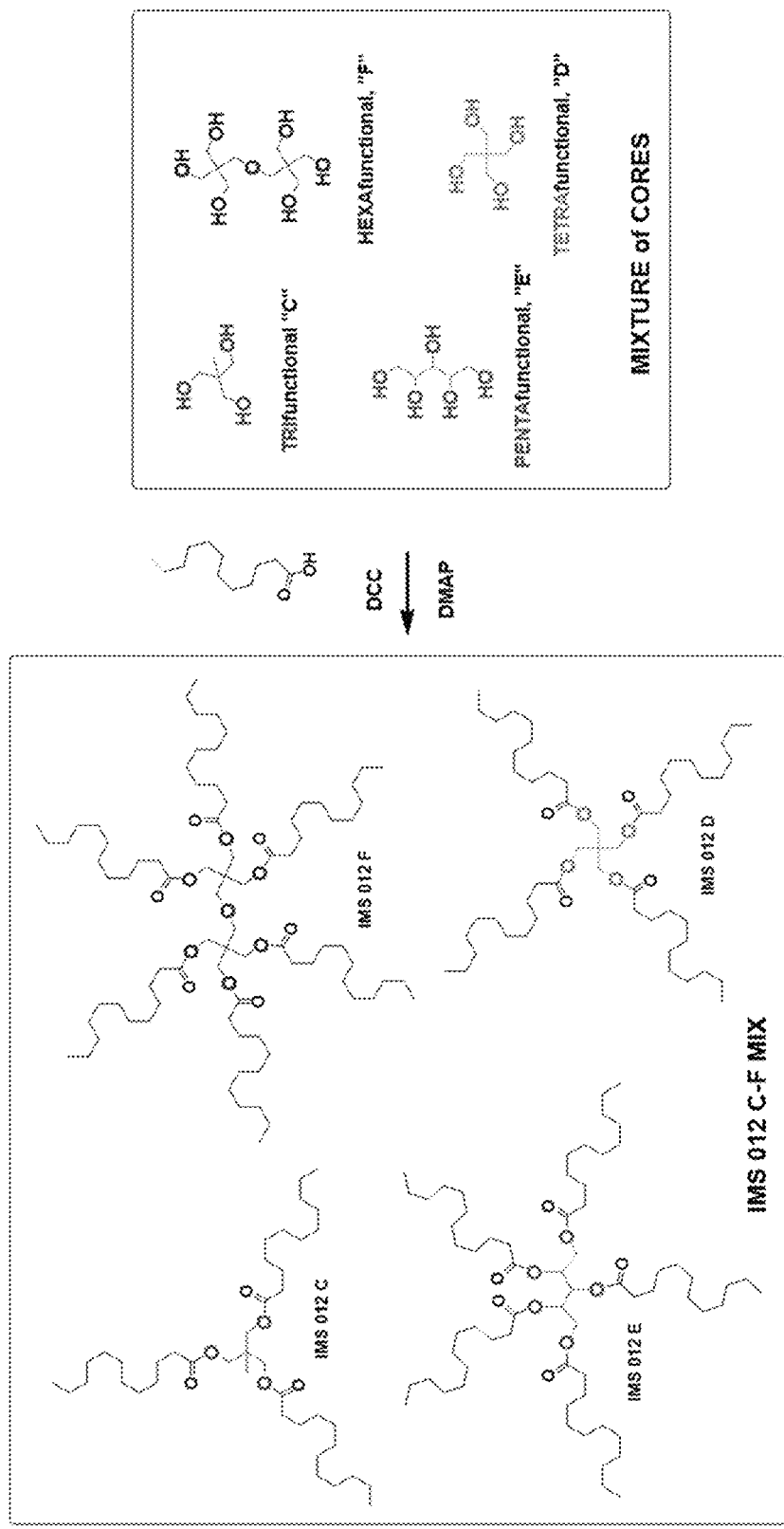
FIG. 9 shows a scheme for the synthesis of calibrants in accordance with an embodiment of the present disclosure.

FIG. 9 shows a scheme for the synthesis of IMS 012 C-F.

To a round bottom flask was added one or more of the following "core" compounds: tris(hydroxymethyl)ethane ("C"), pentaerythritol ("D"), xylitol ("E"), dipentaerythritol ("F") made from the above cores. These were dissolved in tetrahydrofuran. 1.1 molar equivalents (per —OH of the hydroxyl terminated cores or dendrimers) of Dodecanoic Acid were added to the solution of cores. To these reagents were added 1.2 molar equivalents (per —OH of the hydroxyl terminated cores or dendrimers) of dicyclohexylcarbodiimide and 0.1 molar equivalents (per —OH of hydroxyl-terminated core or of dendrimer) of 4-dimethylaminopyridine (DMAP).

The reaction mixture was stirred vigorously for approximately 12 hours at standard temperature and pressure. The reaction was monitored by MALDI-TOF MS to determine completion of the reaction for each of the cores present in the reaction. After complete esterification is observed by MALDI-TOF MS, the flask contents were transferred to a separatory funnel, diluted with dichloromethane, extracted twice with 1M aqueous $NaHSO_4$ (sodium bisulfate) and extracted twice with 1M aqueous $NaHCO_3$ (sodium bicarbonate). The organic layer was reduced in vacuo to concentrate the sample. A MALDI-TOF MS spectra of the purified product confirmed the purity of the mixture of esterified products and is shown in FIG. 10.

Figure 10:
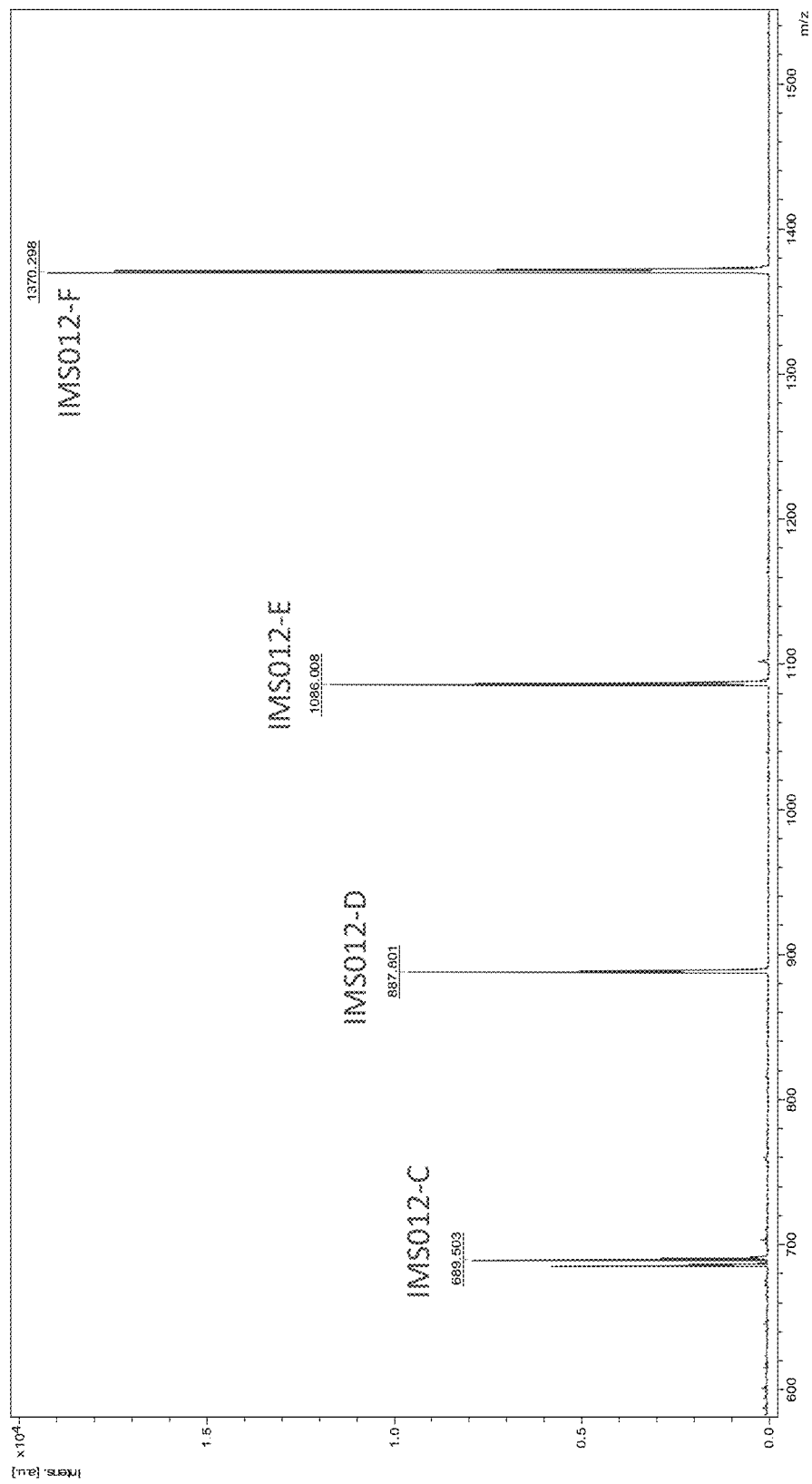
FIG. 10 shows MALDI-TOF MS data for calibrants in accordance with another embodiment of the present disclosure.

FIG. 10 shows MALDI-TOF MS data for IMS 012 C-F, the product of dodecanoic acid functionalization of cores C, D, E, and F.

Example 4

Octadecanoate Functionalized Core (IMS 018 H)

To a round bottom flask was added one or more of the following "core" compounds: tripentaerythritol ("H") made from the above cores. These were dissolved in tetrahydrofuran. 1.1 molar equivalents (per —OH of the hydroxyl terminated cores or dendrimers) of Octadecanoic Acid were added to the solution of cores. To these reagents were added 1.2 molar equivalents (per —OH of the hydroxyl terminated cores or dendrimers) of dicyclohexylcarbodiimide and 0.1 molar equivalents (per —OH of hydroxyl-terminated core or of dendrimer) of 4-dimethylaminopyridine (DMAP).

The reaction mixture was stirred vigorously for approximately 12 hours at standard temperature and pressure. The reaction was monitored by MALDI-TOF MS to determine completion of the reaction for each of the cores present in the reaction. After complete esterification is observed by MALDI-TOF MS, the flask contents were transferred to a separatory funnel, diluted with dichloromethane, extracted twice with 1M aqueous NaHSO$_4$ (sodium bisulfate) and extracted twice with 1M aqueous NaHCO$_3$ (sodium bicarbonate). The organic layer was reduced in vacuo to concentrate the sample. A MALDI-TOF MS spectra of the purified product confirmed the purity of the mixture of esterified products and is shown in FIG. 11.

Figure 11:
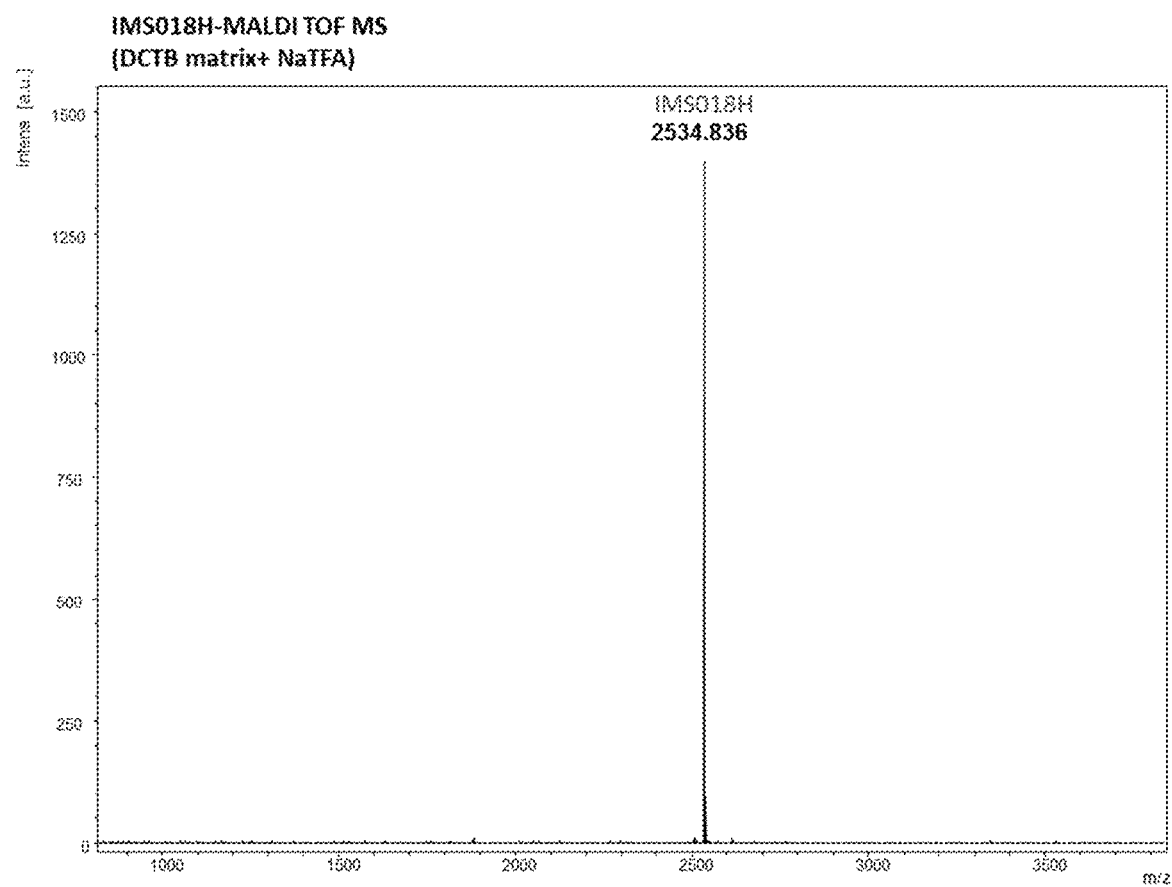
FIG. 11 shows MALDI-TOF MS data for calibrants in accordance with another embodiment the present disclosure.

FIG. 11 shows MALDI-TOF MS data for IMS 018 H, the product of octadecanoic acid functionalization of core H (IMS018H).

Example 5

Octadecanoate Functionalized G1 Dendrimer Cores (IMS 018 C1-F1)

Figure 12:
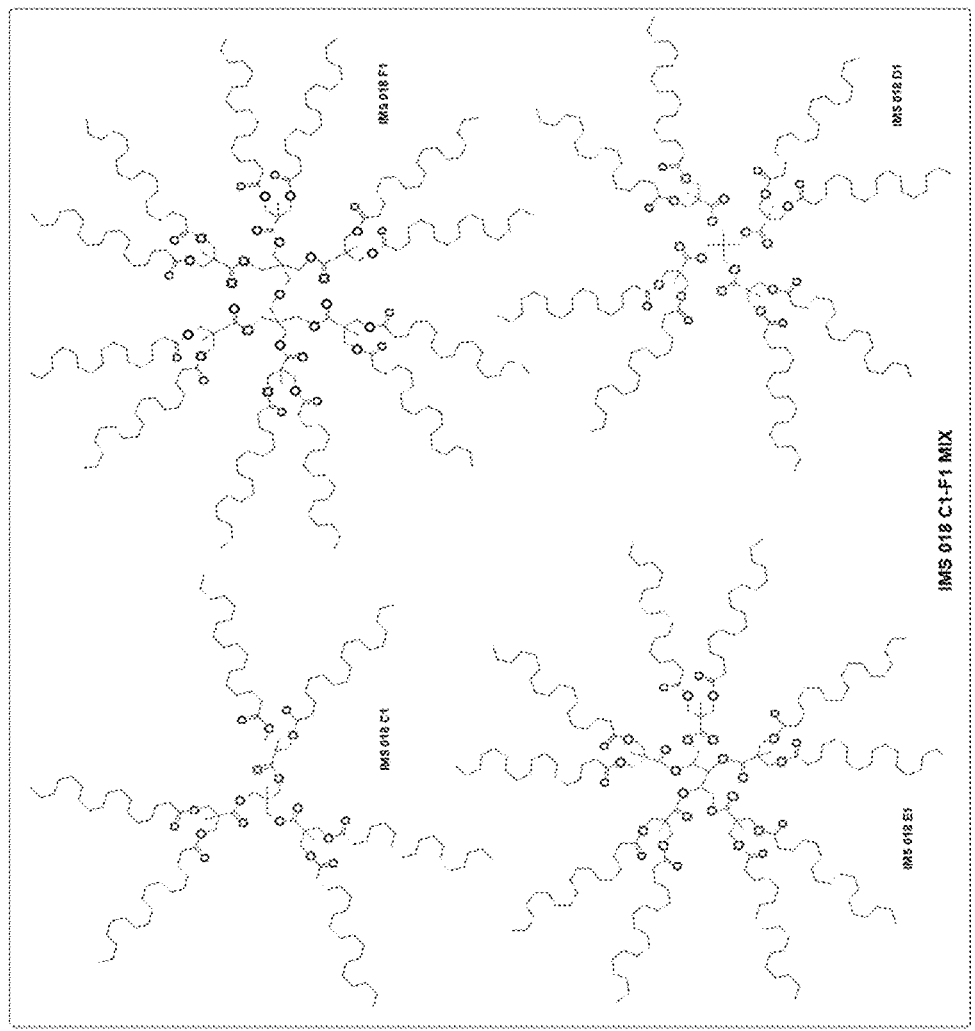
FIG. 12 shows a scheme for the synthesis of calibrants in accordance with another embodiment of the present disclosure.
Figure 12:
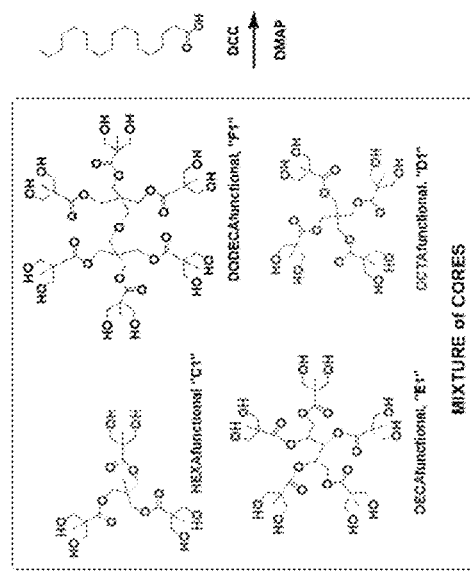

FIG. 12 shows a scheme for the synthesis of IMS 018 C1-F1.

To a round bottom flask was added one or more of the following "core" compounds: the first generation of bis-MPA dendrimers from the following 4 cores: tris(hydroxymethyl)ethane ("C1"), pentaerythritol ("D1"), xylitol ("E1"), dipentaerythritol ("F1") made from the above cores. These were dissolved in tetrahydrofuran. 1.1 molar equivalents (per —OH of the hydroxyl terminated cores or dendrimers) of Octadecanoic Acid were added to the solution of cores. To these reagents were added 1.2 molar equivalents (per —OH of the hydroxyl terminated cores or dendrimers) of dicyclohexylcarbodiimide and 0.1 molar equivalents (per —OH of hydroxyl-terminated core or of dendrimer) of 4-dimethylaminopyridine (DMAP).

The reaction mixture was stirred vigorously for approximately 12 hours at standard temperature and pressure. The reaction was monitored by MALDI-TOF MS to determine completion of the reaction for each of the cores present in the reaction. After complete esterification is observed by MALDI-TOF MS, the flask contents were transferred to a separatory funnel, diluted with dichloromethane, extracted twice with 1M aqueous NaHSO$_4$ (sodium bisulfate) and extracted twice with 1M aqueous NaHCO$_3$ (sodium bicarbonate). The organic layer was reduced in vacuo to concentrate the sample. A MALDI-TOF MS spectra of the purified product confirmed the purity of the mixture of esterified products and is shown in FIG. 13.

Figure 13:
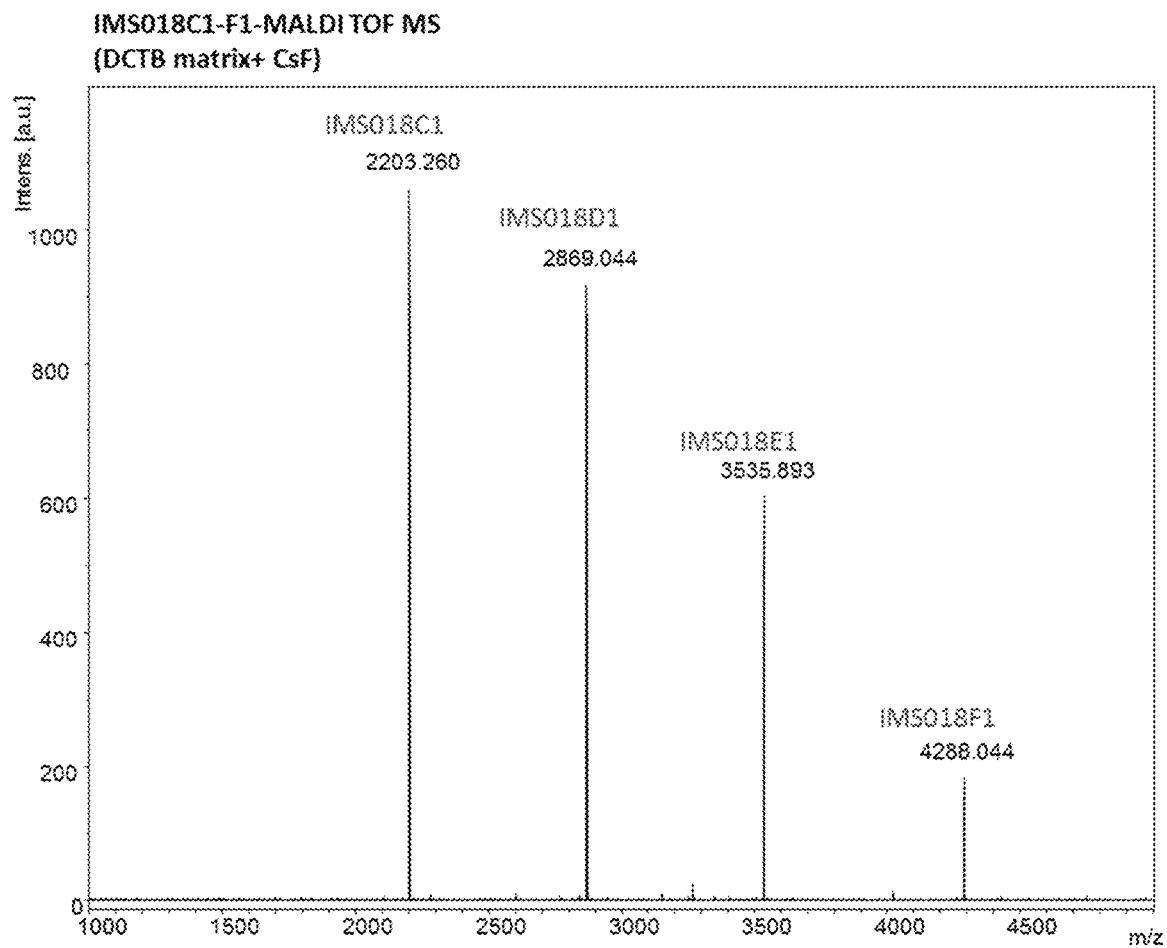
FIG. 13 shows MALDI-TOF MS data for calibrants in accordance with another embodiment of the present disclosure.

FIG. 13 shows MALDI-TOF MS data for IMS 018 C1-F1, the product of octadecanoic acid functionalization of cores C1, D1, E1, and F1.

Example 6

Docosanoate Functionalized Cores (IMS 022 C-F)

To a round bottom flask was added one or more of the following "core" compounds: tris(hydroxymethyl)ethane ("C"), pentaerythritol ("D"), xylitol ("E"), dipentaerythritol ("F") made from the above cores. These were dissolved in tetrahydrofuran. 1.1 molar equivalents (per —OH of the hydroxyl terminated cores or dendrimers) of Docosanoic Acid were added to the solution of cores. To these reagents were added 1.2 molar equivalents (per —OH of the hydroxyl terminated cores or dendrimers) of dicyclohexylcarbodiimide and 0.1 molar equivalents (per —OH of hydroxyl-terminated core or of dendrimer) of 4-dimethylaminopyridine (DMAP).

The reaction mixture was stirred vigorously for approximately 12 hours at standard temperature and pressure. The reaction was monitored by MALDI-TOF MS to determine completion of the reaction for each of the cores present in the reaction. After complete esterification is observed by MALDI-TOF MS, the flask contents were transferred to a separatory funnel, diluted with dichloromethane, extracted twice with 1M aqueous NaHSO$_4$ (sodium bisulfate) and extracted twice with 1M aqueous NaHCO$_3$ (sodium bicarbonate). The organic layer was reduced in vacuo to concentrate the sample. A MALDI-TOF MS spectra of the purified product confirmed the purity of the mixture of esterified products and is shown in FIG. 14.

Figure 14:
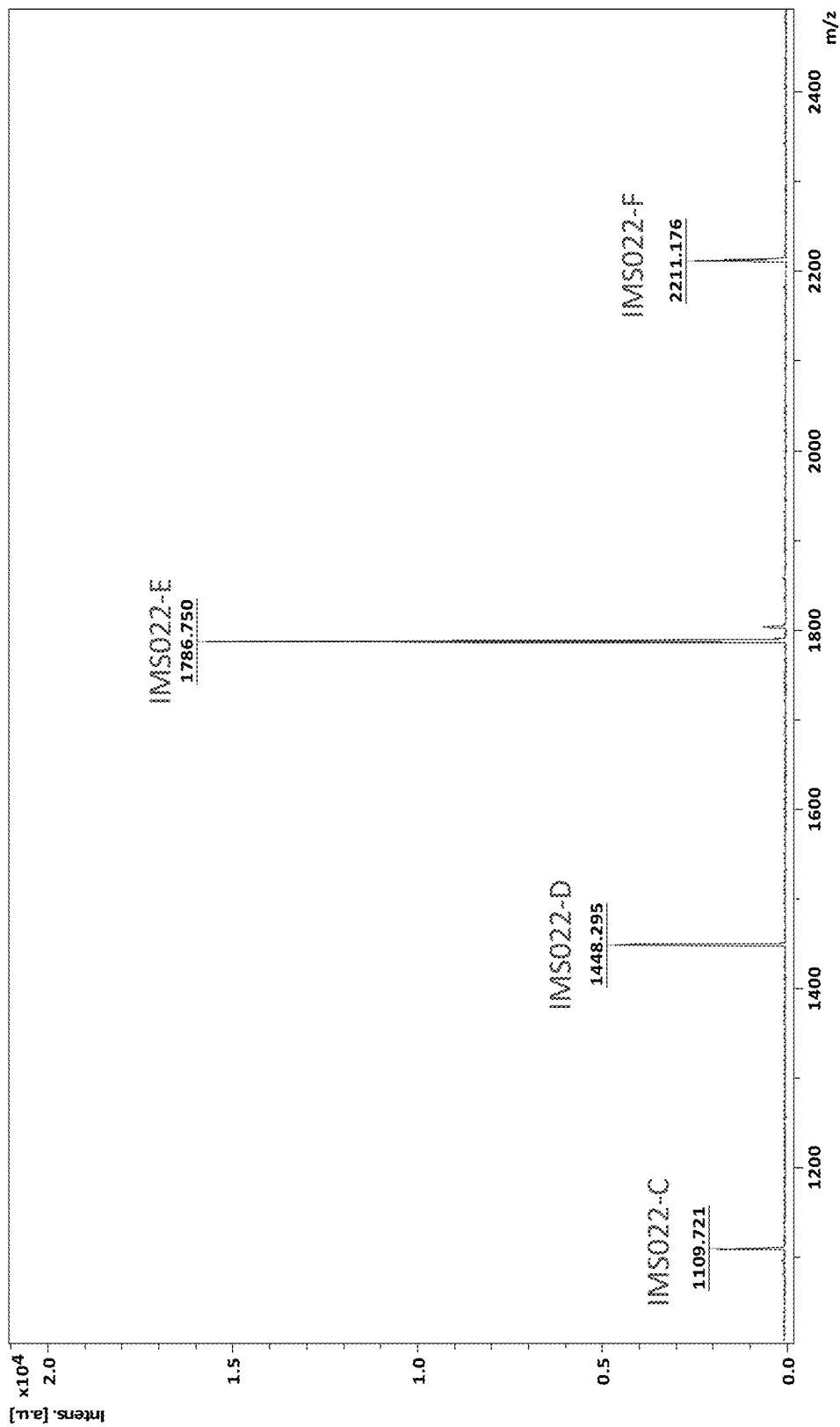
FIG. 14 shows MALDI-TOF MS data for calibrants in accordance with another embodiment of the present disclosure.

FIG. 14 shows MALDI-TOF MS data for IMS 022 C-F, the product of docosanoic acid functionalization of cores C, D, E, and F.

Example 7

Benzoate Functionalized Cores (IMS 100 C-F)

To a round bottom flask was added one or more of the following "core" compounds: tris(hydroxymethyl)ethane ("C"), pentaerythritol ("D"), xylitol ("E"), dipentaerythritol ("F") made from the above cores. These were dissolved in tetrahydrofuran. 1.1 molar equivalents (per —OH of the hydroxyl terminated cores or dendrimers) of Benzoic Acid were added to the solution of cores. To these reagents were added 1.2 molar equivalents (per —OH of the hydroxyl terminated cores or dendrimers) of dicyclohexylcarbodiimide and 0.1 molar equivalents (per —OH of hydroxyl-terminated core or of dendrimer) of 4-dimethylaminopyridine (DMAP).

The reaction mixture was stirred vigorously for approximately 12 hours at standard temperature and pressure. The reaction was monitored by MALDI-TOF MS to determine completion of the reaction for each of the cores present in the reaction. After complete esterification is observed by MALDI-TOF MS, the flask contents were transferred to a separatory funnel, diluted with dichloromethane, extracted twice with 1M aqueous NaHSO$_4$ (sodium bisulfate) and extracted twice with 1M aqueous NaHCO$_3$ (sodium bicarbonate). The organic layer was reduced in vacuo to concentrate the sample. A MALDI-TOF MS spectra of the purified product confirmed the purity of the mixture of esterified products and is shown in FIG. 15.

Figure 15:
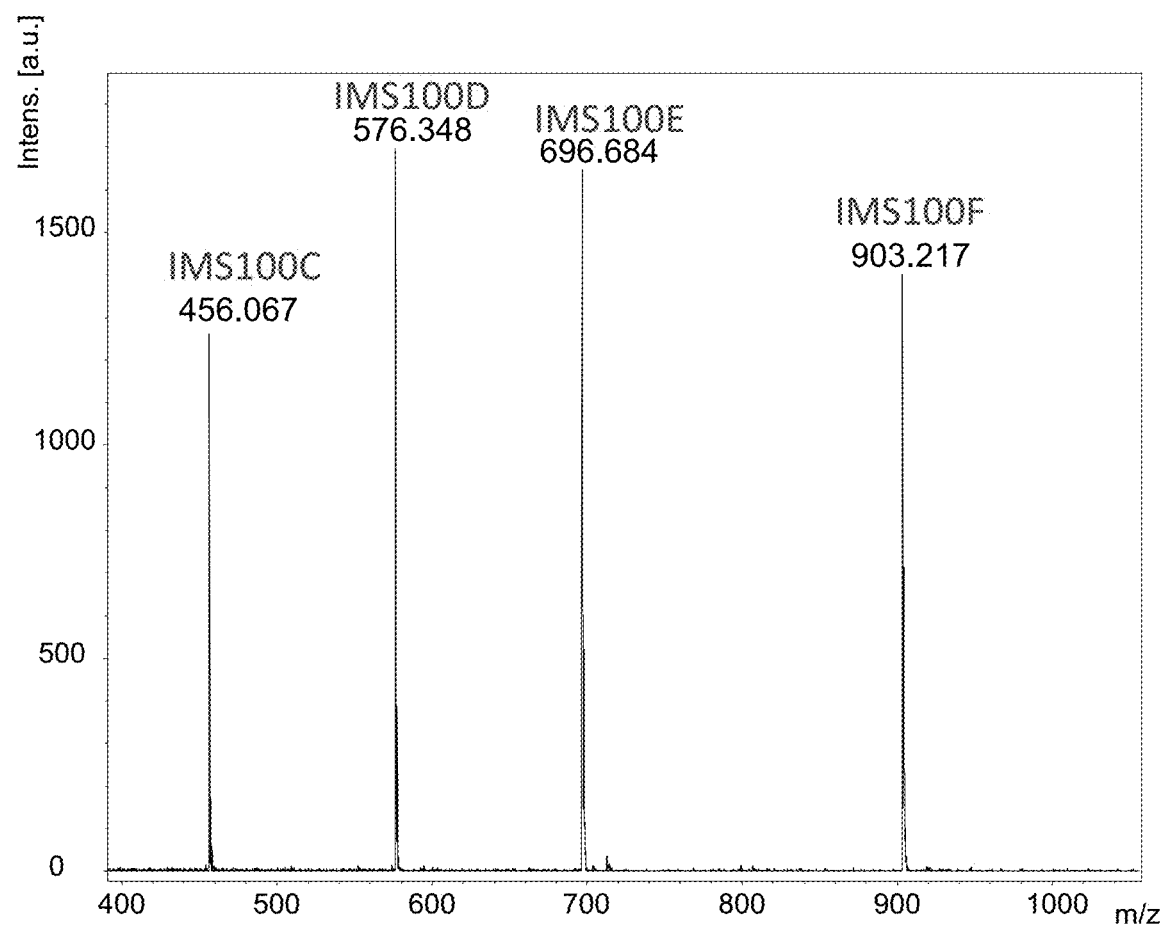
FIG. 15 shows MALDI-TOF MS data for calibrants in accordance with another embodiment of the present disclosure.

FIG. 15 shows MALDI-TOF MS data for IMS 100 C-F, the product of benzoic acid functionalization of cores C, D, E, and F.

Example 8

Triiodobenzoate Functionalized Cores (IMS 103 C-F)

Figure 16:
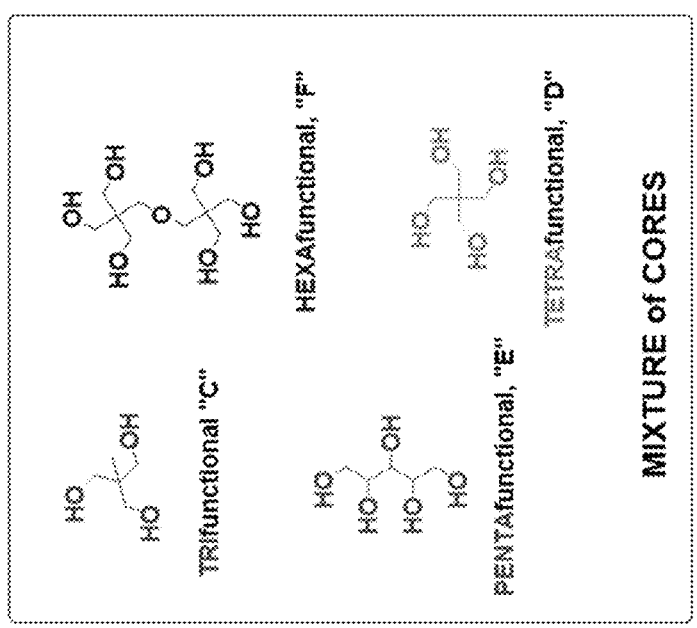
FIG. 16 shows a scheme for the synthesis of calibrants in accordance with another embodiment of the present disclosure.
Figure 16:
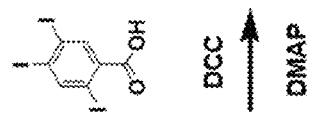
Figure 16:
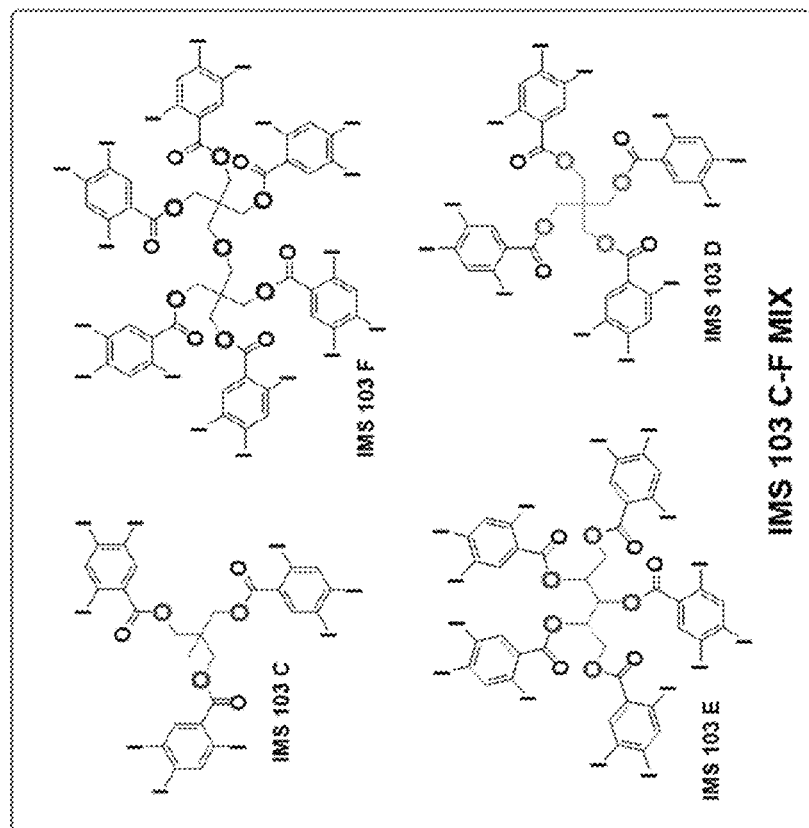

FIG. 16 shows a scheme for the synthesis of IMS 103 C-F.

To a round bottom flask was added one or more of the following "core" compounds: tris(hydroxymethyl)ethane ("C"), pentaerythritol ("D"), xylitol ("E"), dipentaerythritol ("F") made from the above cores. These were dissolved in tetrahydrofuran. 1.1 molar equivalents (per —OH of the hydroxyl terminated cores or dendrimers) of Triiodobenzoic Acid were added to the solution of cores. To these reagents were added 1.2 molar equivalents (per —OH of the hydroxyl terminated cores or dendrimers) of dicyclohexylcarbodiimide and 0.1 molar equivalents (per —OH of hydroxyl-terminated core or of dendrimer) of 4-dimethylaminopyridine (DMAP).

The reaction mixture was stirred vigorously for approximately 12 hours at standard temperature and pressure. The reaction was monitored by MALDI-TOF MS to determine completion of the reaction for each of the cores present in the reaction. After complete esterification is observed by MALDI-TOF MS, the flask contents were transferred to a separatory funnel, diluted with dichloromethane, extracted twice with 1M aqueous $NaHSO_4$ (sodium bisulfate) and extracted twice with 1M aqueous $NaHCO_3$ (sodium bicarbonate). The organic layer was reduced in vacuo to concentrate the sample. A MALDI-TOF MS spectra of the purified product confirmed the purity of the mixture of esterified products and is shown in FIG. 17.

Figure 17:
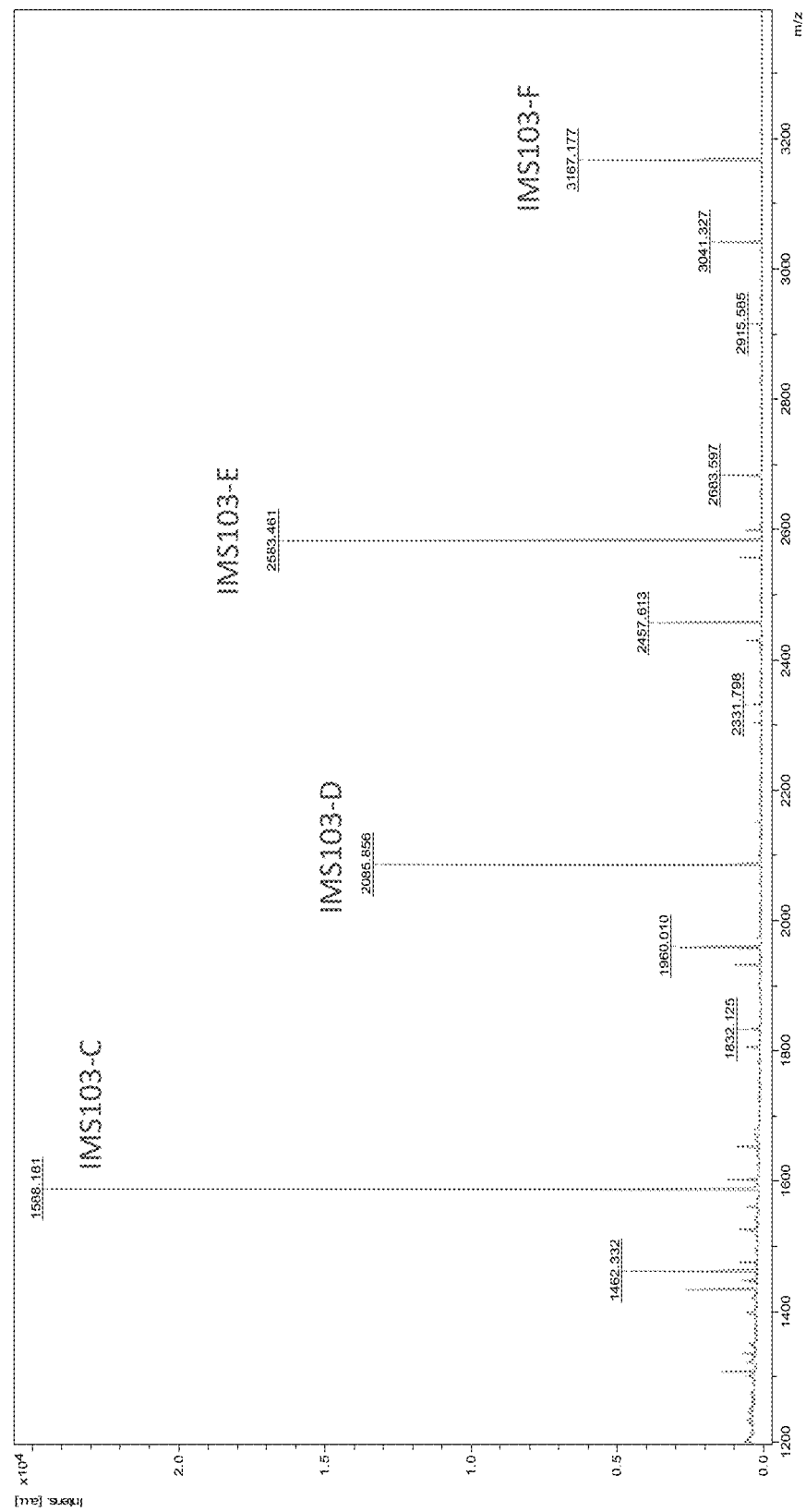
FIG. 17 shows MALDI-TOF MS data for calibrants in accordance with another embodiment of the present disclosure.

FIG. 17 shows MALDI-TOF MS data for IMS 103 C-F, the product of triiodobenzoic acid functionalization of cores C, D, E, and F.

Example 9

Triiodobenzoate Functionalized Cores (IMS 103 H)

To a round bottom flask was added one or more of the following "core" compounds: tripentaerythritol ("H") made from the above cores. These were dissolved in tetrahydrofuran. 1.1 molar equivalents (per —OH of the hydroxyl terminated cores or dendrimers) of Triiodobenzoic Acid were added to the solution of cores. To these reagents were added 1.2 molar equivalents (per —OH of the hydroxyl terminated cores or dendrimers) of dicyclohexylcarbodiimide and 0.1 molar equivalents (per —OH of hydroxyl-terminated core or of dendrimer) of 4-dimethylaminopyridine (DMAP).

The reaction mixture was stirred vigorously for approximately 12 hours at standard temperature and pressure. The reaction was monitored by MALDI-TOF MS to determine completion of the reaction for each of the cores present in the reaction. After complete esterification is observed by MALDI-TOF MS, the flask contents were transferred to a separatory funnel, diluted with dichloromethane, extracted twice with 1M aqueous $NaHSO_4$ (sodium bisulfate) and extracted twice with 1M aqueous $NaHCO_3$ (sodium bicarbonate). The organic layer was reduced in vacuo to concentrate the sample. A MALDI-TOF MS spectra of the purified product confirmed the purity of the mixture of esterified products and is shown in FIG. 18.

Figure 18:
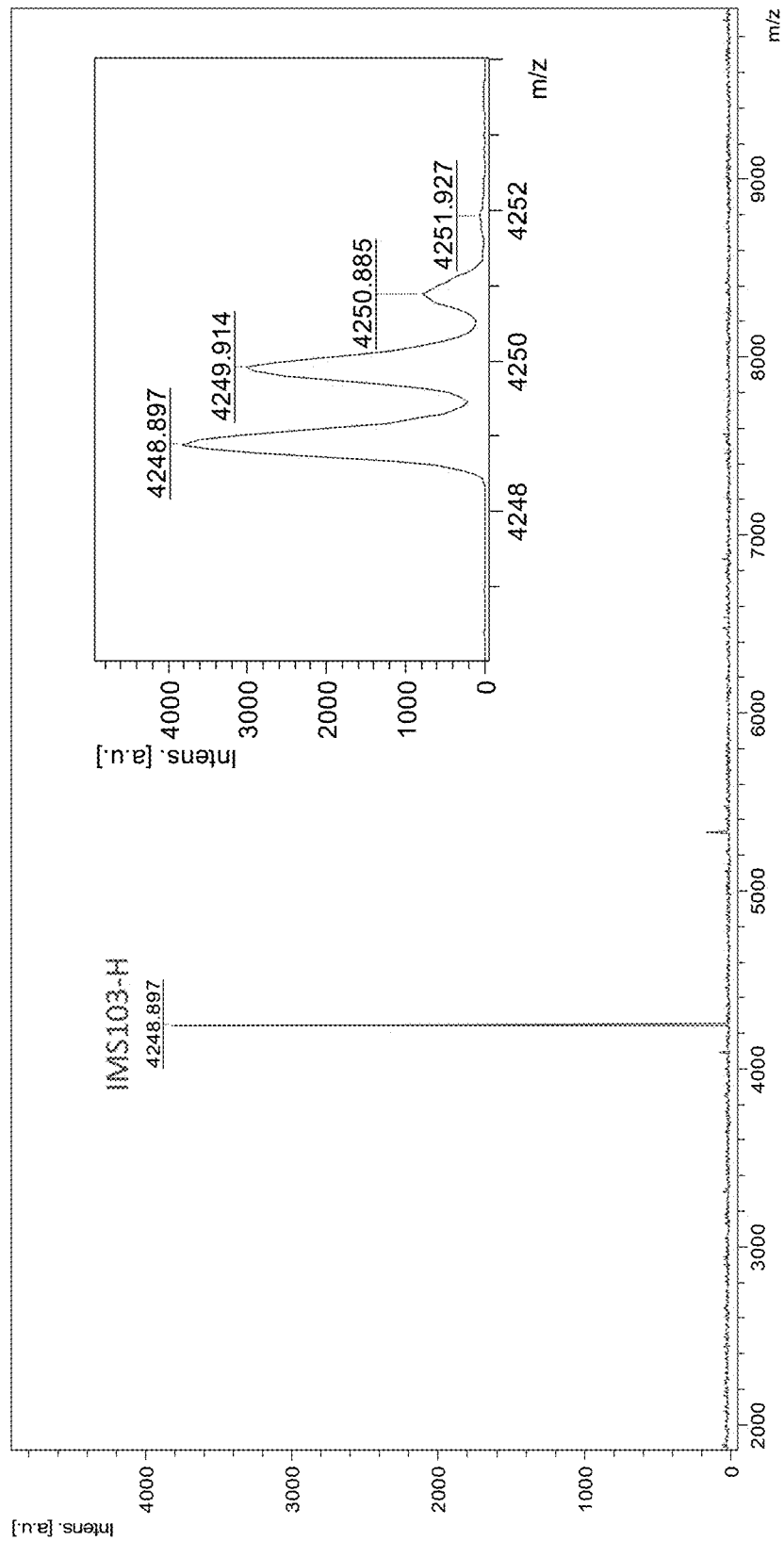
FIG. 18 shows MALDI-TOF MS data for calibrants in accordance with another embodiment of the present disclosure.

FIG. 18 shows MALDI-TOF MS data for IMS 004 H, the product of triiodobenzoic acid functionalization of core H.

Example 10

Triiodobenzoate Functionalized G1 Dendrimer Cores (IMS 103 C1-F1)

Figure 19:
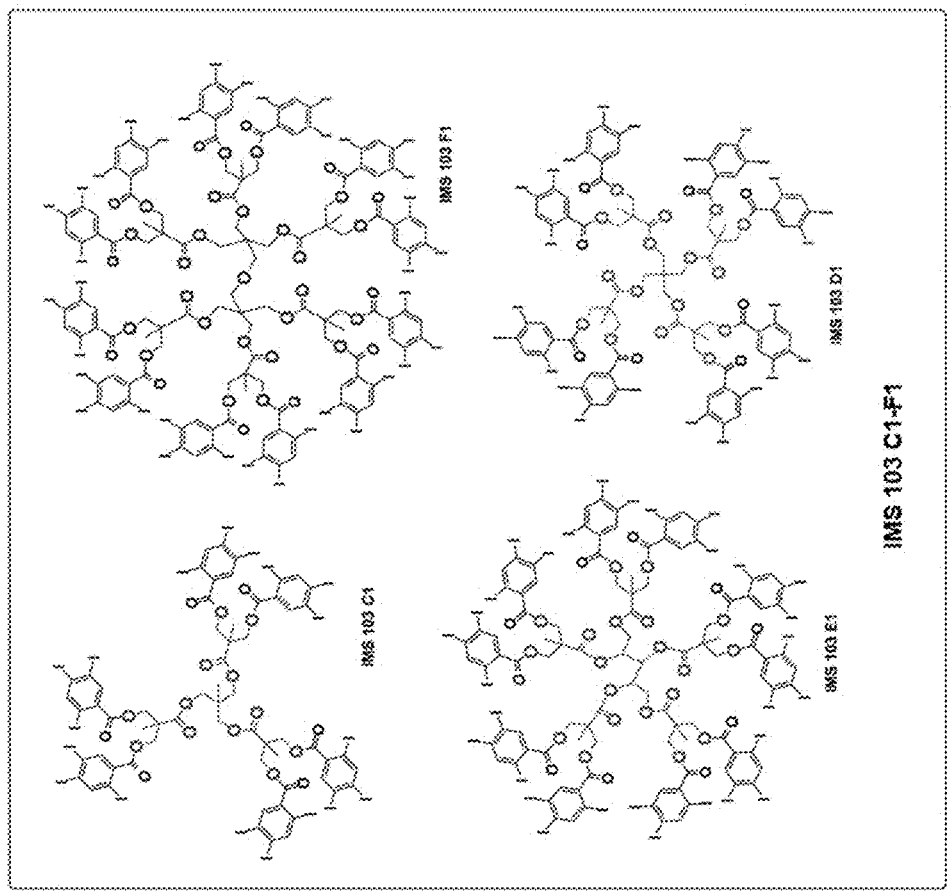
FIG. 19 shows a scheme for the synthesis of calibrants in accordance with another embodiment of the present disclosure.
Figure 19:
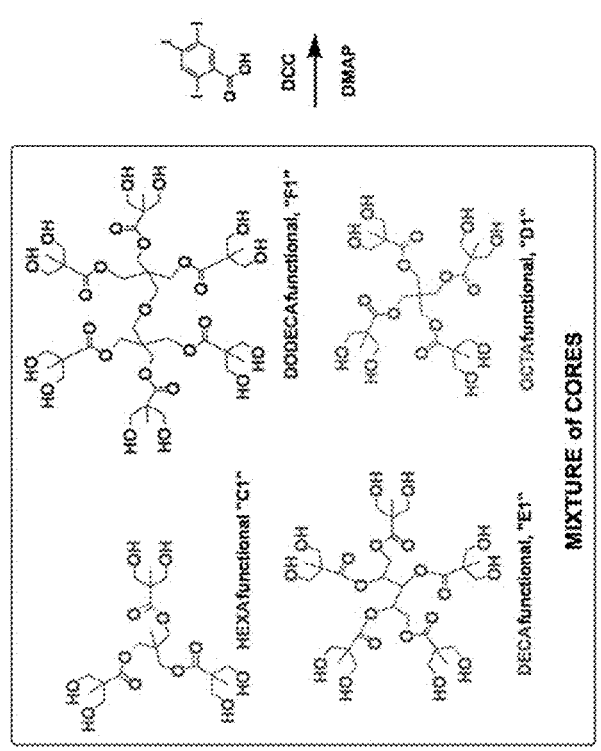

FIG. 19 shows a scheme for the synthesis of IMS 103 C1-F1.

To a round bottom flask was added one or more of the following "core" compounds: the first generation of bis-MPA dendrimers from the following 4 cores: tris(hydroxymethyl)ethane ("C1"), pentaerythritol ("D1"), xylitol ("E1"), dipentaerythritol ("F1") made from the above cores. These were dissolved in tetrahydrofuran. 1.1 molar equivalents (per —OH of the hydroxyl terminated cores or dendrimers) of Triiodobenzoic Acid are added to the solution of cores. To these reagents were added 1.2 molar equivalents (per —OH of the hydroxyl terminated cores or dendrimers) of dicyclohexylcarbodiimide and 0.1 molar equivalents (per —OH of hydroxyl-terminated core or of dendrimer) of 4-dimethylaminopyridine (DMAP).

The reaction mixture was stirred vigorously for approximately 12 hours at standard temperature and pressure. The reaction was monitored by MALDI-TOF MS to determine completion of the reaction for each of the cores present in the reaction. After complete esterification is observed by MALDI-TOF MS, the flask contents were transferred to a separatory funnel, diluted with dichloromethane, extracted twice with 1M aqueous $NaHSO_4$ (sodium bisulfate) and extracted twice with 1M aqueous $NaHCO_3$ (sodium bicarbonate). The organic layer was reduced in vacuo to concentrate the sample. A MALDI-TOF MS spectra of the purified product confirmed the purity of the mixture of esterified products and is shown in FIG. 20.

Figure 20:
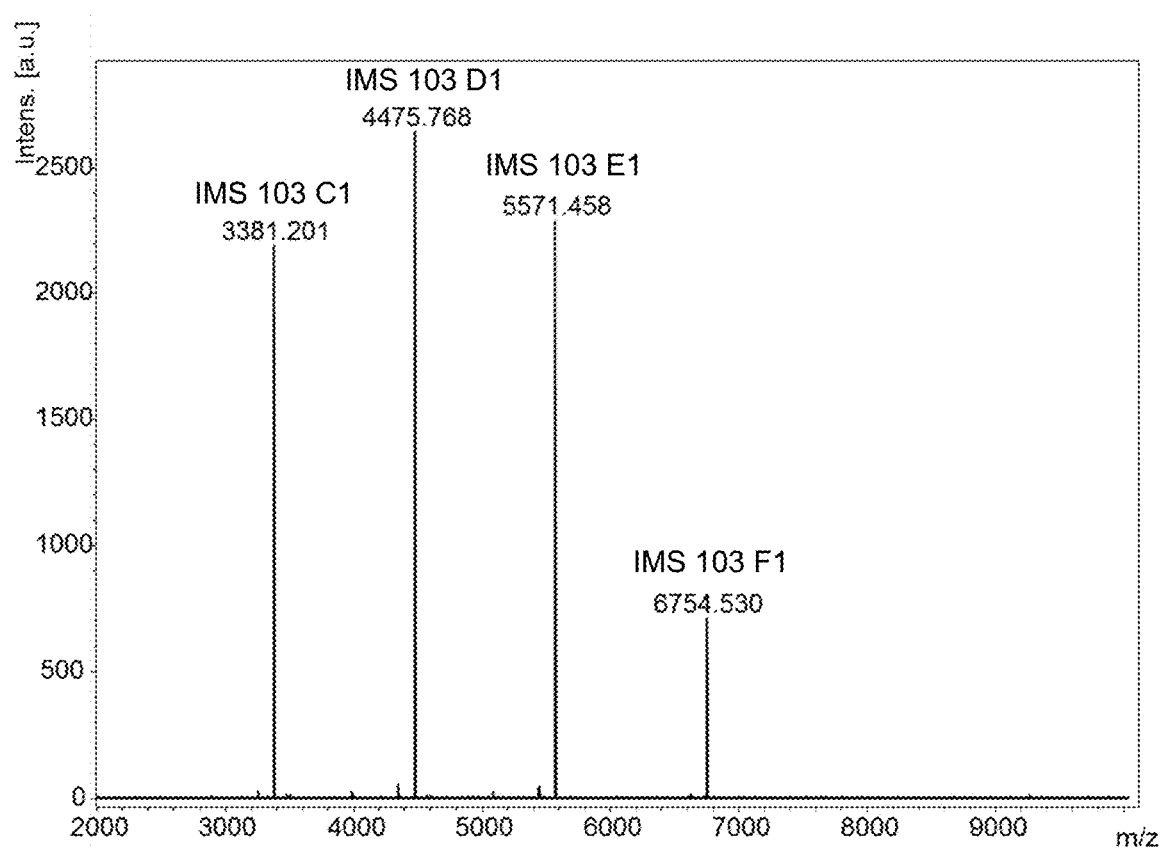
FIG. 20 shows MALDI-TOF MS data for calibrants in accordance with another embodiment of the present disclosure.

FIG. 20 shows MALDI-TOF MS data for IMS 103 C1-F1, the product of triiodobenzoate acid functionalization of cores C1, D1, E1 and F1.

Example 11

Triiodobenzoate Functionalized Amine Cores

Figure 21:
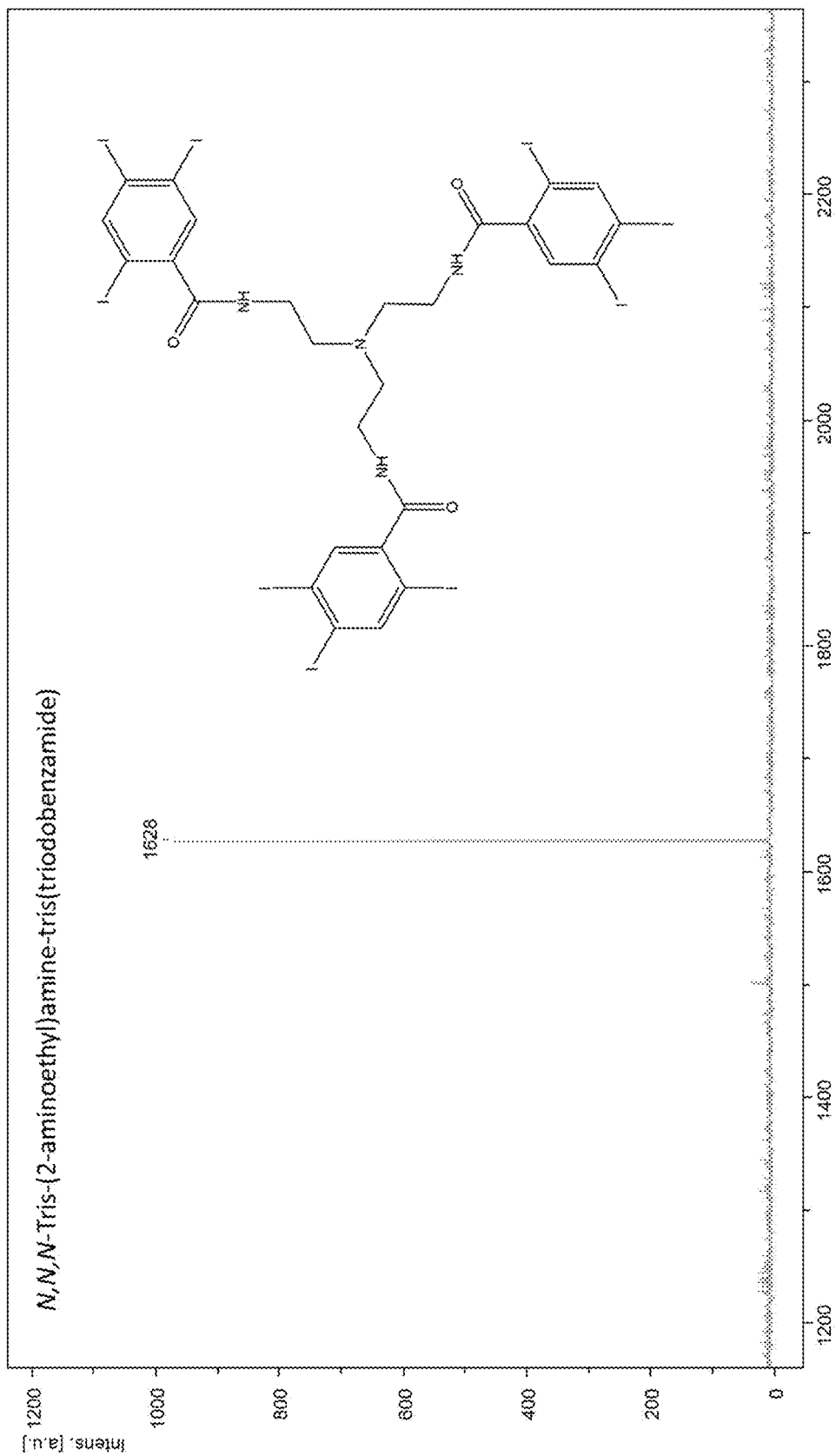
FIG. 21 shows MALDI-TOF MS data for calibrants in accordance with another embodiment of the present disclosure.

FIG. 21 shows the MALDI-TOF mass spectrum for the product, i.e., N,N,N-Tris-(2-aminoethyl)amine-tris(triiodobenzamide) or N,N',N"-(nitrilotris(ethane-2,1-diyl))tris(2,3,5-triiodobenzamide) of the amidation reaction between N,N,N-tris(2-aminoethyl)amine and 2,3,5-triiodobenzoic acid.

Example 12

Stability of IMS Calibrants

Figure 22:
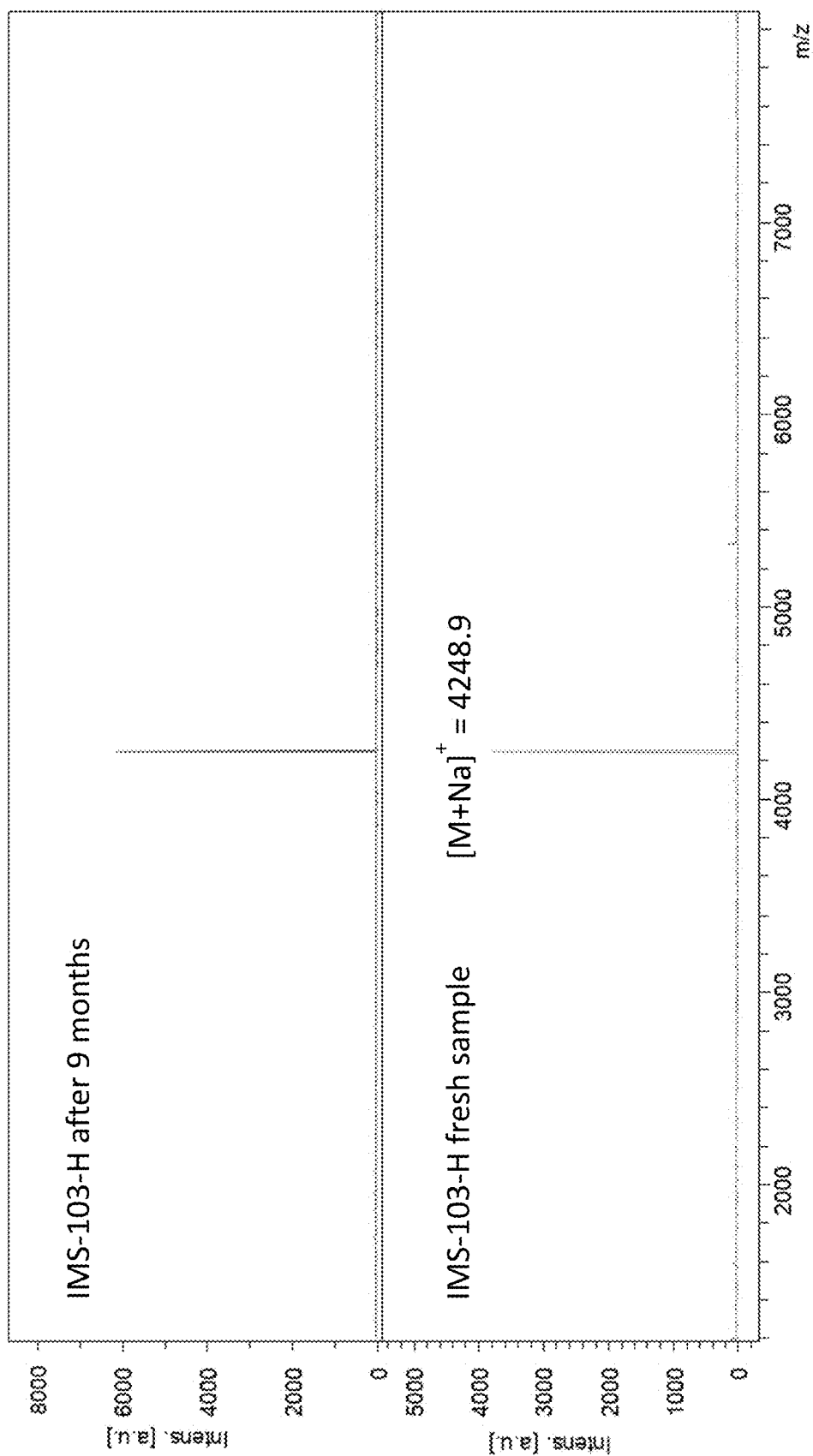
FIG. 22 shows stability of calibrants in accordance with an embodiment of the present disclosure.

FIG. 22 shows representative example of stability of IMS calibrants under ambient conditions—IMS 103 H at 0 months (bottom panel) and after 9 months (top panel) of storage. This data shows after 9 months at ambient conditions (e.g., exposed to room temperature, light, and air), no sign of degradation of these calibrants was observed.

Advantages of the present disclosure include calibrant compounds exhibiting a range of compactness, from high CCS with low m/z (more extended) to low CCS with high m/z (more compact). These compounds may serve as calibration points that cover a larger area of the ion mobility-mass spectrometry graph. The compactness of the calibrants may be tuned (e.g. varying peripheral groups from long, extended linear fatty acids, to short, mass-dense iodinated aromatic rings) to adjust the range of values on the x-axis (e.g. m/z) relative to those on the y-axis (e.g. CCS) in ion mobility-mass spectrometry spectra in order to improve the quality of calibration. Thus, these calibrants may be used in a variety of analytical instruments, in addition to IM-MS, e.g., in a mass spectrometer, an ion mobility spectrometer, a light scattering spectrometer, and a size exclusion chromatograph.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A composition comprising at least two calibrant compounds or salts thereof, or cationic complexes thereof, or anionic complexes thereof, wherein the at least two calibrant compounds or the salts thereof or the cationic complexes thereof, or the anionic complexes thereof comprise an alcohol functionalized core, and peripheral functionalities, wherein the at least two cores with at least one alcohol functionality is selected from the group consisting of:

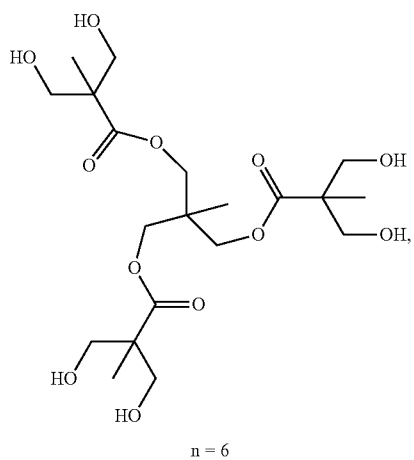

C1 n = 6

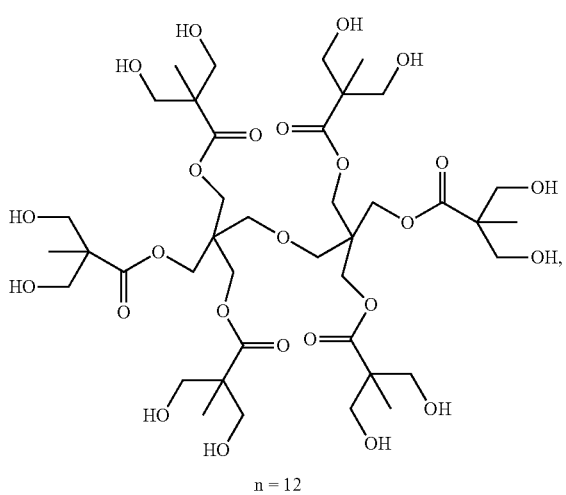

F1 n = 12

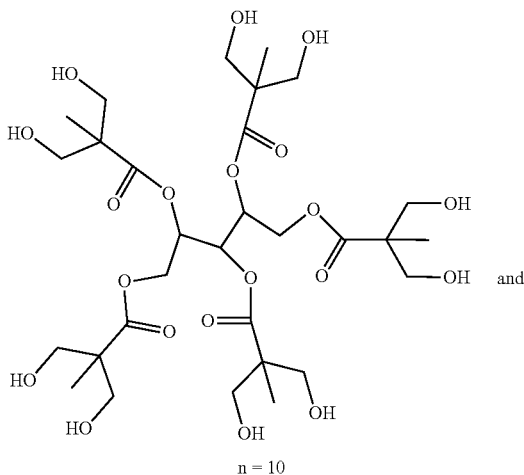

E1 n = 10 and

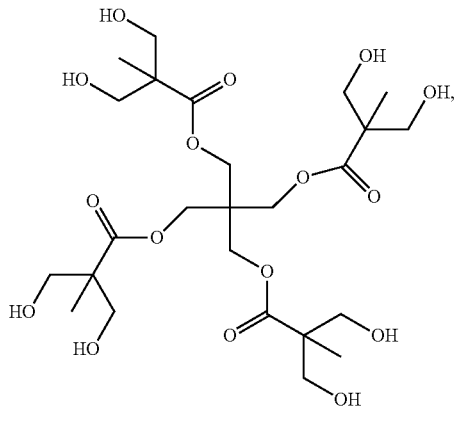

D1 n = 8 and wherein the peripheral functionalities are esters prepared by coupling the alcohol functionalities of the cores with a carboxylic acid, or an activated ester, or an activated carboxylic acid derivative having a chemical structure of Formula II:

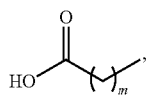

(Formula II)

wherein m=1-30.

2. The composition of claim 1, wherein the peripheral functionalities are esters prepared by coupling the alcohol functionalities of the cores with a carboxylic acid selected from the group consisting of methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosenoic acid, tetracosanoic acid, hexacosanoic acid, octacosanoic acid, and triacosanoic acid.

3. A method of manufacturing the composition of claim 1, comprising
mixing of the at least two cores with at least one alcohol functionality, and
subjecting the mixture to an esterification reaction.

4. A method of calibrating an instrument, comprising
providing the composition of claim 1,
collecting data from the composition with the instrument, and
calibrating the instrument based on the collected data, wherein the instrument is selected from the group consisting of mass spectrometer, ion mobility spectrometer, ion mobility-mass spectrometer, light scattering spectrometer, size exclusion chromatograph, and a combination thereof.

5. A method of determining physical properties of a sample, comprising providing the composition of claim 1,
providing the sample,
collecting physical data from the at least one calibrant compound,
calibrating an instrument capable of measuring the physical properties based on the physical data, and
determining the physical properties of the sample.

6. The method of claim 5, wherein the physical properties of the sample comprise mass, size, shape, and/or collisional cross section area of the sample in a drift gas.

7. The method of claim 5, wherein the instrument is selected from the group consisting of mass spectrometer, ion mobility spectrometer, ion mobility-mass spectrometer, light scattering spectrometer, size exclusion chromatograph, and a combination thereof.

8. The composition of claim 2, wherein the carboxylic acid is methanoic acid.

9. The composition of claim 2, wherein the carboxylic acid is ethanoic acid.

10. The composition of claim 2, wherein the carboxylic acid is propanoic acid.

11. The composition of claim 2, wherein the carboxylic acid is butanoic acid.

12. The composition of claim 2, wherein the carboxylic acid is hexanoic acid.

13. The composition of claim 2, wherein the carboxylic acid is octanoic acid.

14. The composition of claim 2, wherein the carboxylic acid is decanoic acid.

15. The composition of claim 2, wherein the carboxylic acid is dodecanoic acid.

16. The composition of claim 2, wherein the carboxylic acid is tetradecanoic acid.

17. The composition of claim 2, wherein the carboxylic acid is hexadecanoic acid.

18. The composition of claim 2, wherein the carboxylic acid is octadecanoic acid.

19. The composition of claim 2, wherein the carboxylic acid is eicosanoic acid.

20. The composition of claim 2, wherein the carboxylic acid is docosenoic acid.

* * * * *